US006511804B1

United States Patent
Haydock et al.

(10) Patent No.: US 6,511,804 B1
(45) Date of Patent: Jan. 28, 2003

(54) SELECTIVE ASSAY FOR DETERMINING THE IDENTITY OF LIVE MICROORGANISMS IN A MIXED CULTURE

(75) Inventors: Paul V. Haydock, Seattle; Jack R. Uren, Kirkland, both of WA (US)

(73) Assignee: Saigene Corporation, Seattle, WA (US)

( * ) Notice: Subject to any disclaimer, the term of this patent is extended or adjusted under 35 U.S.C. 154(b) by 0 days.

(21) Appl. No.: 09/647,133
(22) PCT Filed: Mar. 25, 1999
(86) PCT No.: PCT/US99/06610
§ 371 (c)(1),
(2), (4) Date: Jan. 5, 2001
(87) PCT Pub. No.: WO99/50441
PCT Pub. Date: Oct. 7, 1999

Related U.S. Application Data
(60) Provisional application No. 60/079,684, filed on Mar. 27, 1998.

(51) Int. Cl.$^7$ ............................ C12Q 1/68; C12Q 1/18; C12Q 1/04; C12Q 1/02; G01N 33/53
(52) U.S. Cl. .................. 435/6; 435/7.1; 435/29; 435/32; 435/34; 435/91.2; 536/25.32; 536/25.4
(58) Field of Search .................. 435/6, 7.1, 29, 435/32, 34, 91.2; 530/387.1; 536/24.32, 24.33, 25.32, 25.4

(56) References Cited

U.S. PATENT DOCUMENTS

| | | | |
|---|---|---|---|
| 4,416,995 A | 11/1983 | Amaral .................... 435/291 |
| 4,780,406 A | 10/1988 | Dolbeare et al. ............... 435/6 |
| 4,812,394 A | * 3/1989 | Dolbeare et al. ............... 435/6 |
| 5,648,227 A | * 7/1997 | Basboll .................... 435/7.32 |

OTHER PUBLICATIONS

Jou, N–T. et al. J. Clin. Microbiol. 35(5):1161–1165 (May 1997).*

Kell, W. M. et al. Meth. Mol. Cell. Biol. 5(2):105–111 (1995).*

Ahern, H. The Scientist 9(15):20 (Jul. 1995).*

Boehringer Mannheim Catalog "Cell Biology and Immunochemistry: Cell Proliferation, Cytotoxicity, and Cell Death," Chapter 2, Catalog Nos. 1 647 229 & 1 585 045, pp. 213–222.

* cited by examiner

Primary Examiner—Carla J. Myers
Assistant Examiner—Diana Johannsen
(74) Attorney, Agent, or Firm—Townsend and Townsend and Crew, LLP

(57) ABSTRACT

The invention provides a method for determining the identity of an unknown live microorganism in a mixed culture. The microorganism can be a bacterium, fungus, virus, or protozoan. The invention further provides an assay for determining the ability of a selected microorganism in a mixed culture to replicate in the presence of a chemical agent. Kits for determining the identity of a live microorganism in a mixed culture and for determining the ability of a microorganism in a mixed culture to replicate are also provided.

27 Claims, 6 Drawing Sheets

US 6,511,804 B1

SELECTIVE ASSAY FOR DETERMINING THE IDENTITY OF LIVE MICROORGANISMS IN A MIXED CULTURE

CROSS REFERENCE TO RELATED APPLICATIONS

This application is a national stage filing under 35 U.S.C. §371 of PCT/US99/06610, filed Mar. 25, 1999, which claims the benefit of U.S. Provisional Application No. 60/079,684, filed Mar. 27, 1998, the contents of which are incorporated by reference.

BACKGROUND OF THE INVENTION

For decades, scientists have attempted to improve the control of infection and the detection of microorganisms. Determining the susceptibility of microorganisms to particular chemical agents has particular importance in clinical medicine, where the practitioner needs to determine not only which of a number of possible microorganisms might be causing the patient's infection, but also to which agents the particular strain infecting the patient is susceptible. This effort may be complicated or even confounded by the presence of normal flora (bacteria which are usually present at certain body locations, but which do not cause disease under normal conditions) or of other microorganisms which happen to be present but which are not the causative agent of the patient's primary disease. Thus, the determination of both the identity of the organisms present in a sample, and the viability of the target organism, is important. As a practical matter, however, the practitioner often cannot risk a decline in the patient's condition while the organisms present are cultured, identified, and tested for antibiotic susceptibility by conventional techniques, and usually selects a broad spectrum agent in the hope it will be effective against the microorganism actually causing the disease.

A number of techniques are known in the art for determining the viability of microorganisms. These techniques generally permit replication of any microorganisms present and therefore require the use of isolated, pure cultures to give meaningful results. For example, U.S. Pat. No. 4,416,995 teaches a method of determining sensitivity of bacteria to chemical agents by measuring the amount of tritiated thymidine which is incorporated into bacteria in the presence of the agent compared to that incorporated into a second culture in the absence of the agent. In U.S. Pat. No. 4,812,394, Dolbeare et al. teach a non-radioactive technique using the simultaneous measurement by flow cytometry of total cellular DNA and incorporated nucleoside analogs. Cells are permitted to grow in the presence of a nucleoside analog, such as 5-bromodeoxyuridine ("BrdU"), and a portion of the double stranded DNA is then made single stranded. That portion is then "stained" by immunochemical means, such as by antibodies to the nucleoside analog. The unaltered, double stranded DNA is then detected by a stain specific for the unaltered DNA, such as the intercalcating dyes propidium iodide or ethidium bromide.

Antibodies to many nucleotide analogs are commercially available to detect incorporation. ELISA kits are commercially available to measure BrdU uptake into DNA as part of cell viability or proliferation assays. For example, Boehringer Mannheim's "Cell Proliferation ELISA, BrdU" incubates a sample with BrdU. DNA in the sample is then fixed to the wells of a microtiter plate and anti-BrdU antibody-peroxidase conjugate is introduced. The presence of BrdU-labeled DNA is then detected calorimetrically by introduction of tetramethylbenzidine ("TMB") substrate. These methods do not permit the identification of the microorganism, which can be a concern in dealing with the mixed cultures of pathogenic microorganisms and normal microbial flora which are often obtained from patients in clinical situations.

Finally, amplification methods for nucleic acids are known in the art. These methods have the disadvantage of amplifying everything present in a sample. They therefore amplify the nucleic acids of both living and dead microorganisms present in a sample and cannot be used to determine viability of the microorganisms.

SUMMARY OF THE INVENTION

The subject invention discloses an assay for determining the identity of live microorganisms in mixed cultures comprising the steps of (i) culturing the microorganism in a medium comprising a nucleic acid analog recognized by an analog-specific binding member, which is incorporated into nucleic acids of replicating cells of the microorganism, (ii) lysing the microorganism to release its nucleic acids, (iii) capturing nucleic acids incorporating the analog using the analog-specific binding member, (iv) separating the captured nucleic acids from those which were not captured, (v) amplifying the captured nucleic acids using methods selective for particular organisms or groups of organisms, and (vi) detecting the presence or absence of amplified, captured nucleic acids. The amplification can be by polymerase chain reaction.

The invention further discloses that the assay can be used where the microorganism is a pathogen, where the pathogen is a pathogen of a mammal, and where the microorganism is a bacterium, a virus, a fungus, or a protozoan.

Further, the invention can be used to determine the sensitivity of microorganisms in the culture to chemical agents without needing first to isolate the microorganisms.

The invention discloses that the nucleic acid analog can be bromodeoxyuridine. Additionally, the invention discloses that the binding member can be an antibody. Moreover, the analog-binding member can be attached to a solid support.

The invention can further be practiced by repeating the steps at least once (or dividing the medium containing the microorganisms into two aliquots) wherein one of the series of steps (or one of the aliquots) has an antibiotic added to the medium and at least one of the series of steps (or one of the aliquots) does not have an antibiotic added to the medium.

Finally, the invention discloses kits for determining the identity of microorganisms in a mixed culture, or the ability of selected organisms in a mixed culture to replicate, or both, comprising a DNA or RNA analog (depending on the nature of the microorganism of interest) which is recognized by an analog-specific binding member and which is permissive of incorporation into nucleic acids of the microorganism, an analog-specific binding member for capturing nucleic acids incorporating the analog, and instructions for using these components in an assay for determining the ability of microorganisms of interest to replicate.

DESCRIPTION OF THE SPECIFIC EMBODIMENTS

I. INTRODUCTION

Figure 1:
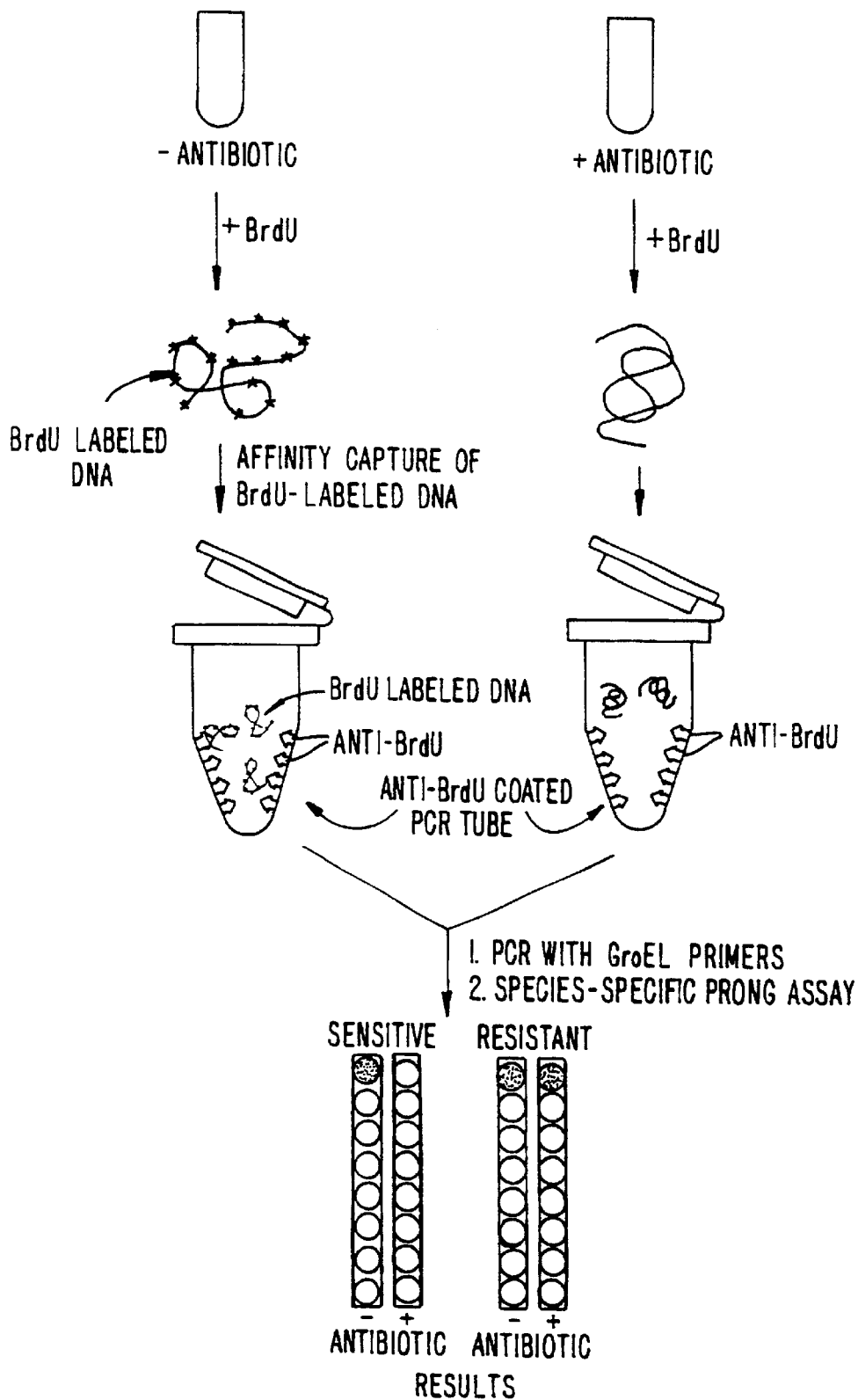
FIG. 1 is a schematic representation showing one method of practicing the invention to detect whether microorganisms in a sample are sensitive to or resistant to an antibiotic. "BrdU" stands for "bromodeoxyuridine." "Anti-BrdU" stands for anti-BrdU antibodies. "GroEL primers" are primers amplifying a gene common to many species of bacteria. The specific primers used are set forth in Table 1, infra.

This invention provides a quick and convenient method not only for determining the presence of living microorganisms in a specimen or sample, but also for identifying the species or strain of those microorganisms. Further, the invention eliminates the need to first separate microorganisms in the sample or specimen into isolated, pure cultures before identifying them. This both eliminates steps and saves time without sacrificing accuracy. The invention does so by combining capture of labeled nucleic acids, physical separation of the captured, labeled nucleic acids from those which are not labeled, and selective amplification. The speed and accuracy of the invention is expected to make it particularly useful in clinical applications.

The invention further permits the use of crude cell or viral lysates. While it is certainly possible to conduct the invention using purified DNA, it is not necessary to do so. This is also expected to save time and expense, both because fewer reagents are needed and because the elimination of purification steps permits a larger number of assays to be conducted over a given period of time. Moreover, since only viable, replicating organisms in the original sample will take up the analog, and only nucleic acids of the target organism (or target group of organisms) will be amplified, the result indicates both whether the target organism was present in the original sample and whether it was viable.

The invention also permits the expedited determination of whether the particular microorganisms, or the particular strain of a microorganism, infecting a patient are sensitive to treatment by particular chemical agents by comparing any differences in the effects of the agent on a test culture compared to a control culture not exposed to the agent. These more rapid determinations are expected to be particularly useful in identifying and determining the appropriate treatment for the specific microorganism causing a patient's infection.

The invention should also be useful in the food preparation and processing industry, where the inability to determine quickly the presence and identity of viable microorganisms in food samples creates delay and increases costs in shipping foods to market. The inability of one meat processing company to demonstrate a break in a line of contamination led to the recent precautionary recall and destruction of millions of pounds of ground beef. The ability to demonstrate the absence of viable pathogens in some of the shipments might have reduced the amount of meat that had to be destroyed.

The need to determine the presence and identity of viable microorganisms is also present in a number of other contexts. Municipalities, for example, often rely on determining the presence or absence of live *E. coli* as a marker for determining if untreated sewage has reached waters accessible from public beaches. Use of this invention permits the rapid determination of the presence of *E. coli*, as well as of pathogens or other microorganisms which might be present.

The basic method of the invention can be set forth briefly as follows, although it is of course more fully described in the discussion below and in the claims. In the simplest form of the method, a sample thought to contain a microorganism is cultured in conditions permitting replication of the microorganism, in the presence of a nucleic acid analog which (1) can be incorporated into nucleic acids of replicating cells (or, if the microorganism is thought to be a virus, replicating virions) of the microorganism, (2) is recognized by a binding member specific for that nucleic acid analog (this can be, for example, an antibody specific recognizing an epitope on that analog, or a compound which has a high affinity for a chemical moiety of the analog), and (3) is permissive of amplification of the nucleic acid The microorganism is then lysed to release nucleic acids, nucleic acids incorporating the analog are captured using the analog-specific binding member, the captured nucleic acids are separated from those not captured by the analog-specific binding member, and the nucleic acids are exposed to conditions permitting selective amplification of nucleic acids from an organism or organisms of interest. The presence or absence of amplified, captured nucleic acids is then detected.

Most commonly, the selective amplification will be by using primers which will amplify only nucleic acids from a particular target organism. Depending on the degree of specificity desired by the practitioner, however, the primers can be degenerate, permitting, depending on the design of the primers, amplification of nucleic acids from a limited family of related organisms or from a fairly wide range.

As noted above, the invention can be utilized to determine whether a microorganism of interest is susceptible or resistant to a chemical agent. Most commonly, the sample is divided, before or after an initial period of culturing, into at least two aliquots, one of which (the "test" sample) contains the chemical agent and one of which (the "control" sample) does not. To facilitate later quantitation, it is usually desirable if the numbers of the microorganisms in the aliquots, and the amount of medium in the aliquots, are roughly equal. The two or more samples are then cultured in the presence of the nucleic acid analogs, the remainder of the steps are taken, and the amounts of nucleic acid incorporating the nucleic acid analog are compared. If the amounts of incorporation are roughly equal, the agent can be determined to have had no or little effect on the growth of that microorganism. If the amount of analog incorporated in the test sample is detectably and significantly below that of the control sample, than it can be said that the chemical agent had an inhibitory effect on the growth of the microorganism. Alternatively, the assay can be conducted by performing the series of steps twice, once without the antibiotic and once with the antibiotic.

The following text sets forth some of the many uses for the invention, and how to practice it. After defining terms and describing uses of the invention, the text discusses the general format of the assay and means to determine whether or not nucleotide analogs have been incorporated into viable microorganisms. It then discusses culturing microorganisms, exemplar nucleic acid analogs and binding agents for those analogs, lysing methods for obtaining access to the microorganism's nucleic acids, and procedures for capturing nucleic acids incorporating the nucleic acid analogs, separation of captured nucleic acids from any which have not been captured, procedures for selectively amplifying microorganisms, and kits for practicing the invention. Finally, examples are set forth to demonstrate use of the invention.

II. DEFINITIONS

As used herein, "microorganism" comprehends bacteria, fungi, protozoa, and viruses. With respect to bacteria, for example, it encompasses mycoplasmas, rickettsiae, and chlamydiae, which replicate within eukaryotic cells, as well as those bacteria which do not. With regard to viruses, it encompasses both DNA and RNA viruses. With respect to fungi, it includes both unicellular forms such as yeasts and the unicellular forms of the dimorphic pathogens. With respect to protozoa it encompasses both organisms which are unicellular and those, such as helminths, which are multicellular, so long as the organism can be cultured in the presence of and incorporate into nucleic acids a nucleotide analog. More generally, the term refers to organisms which can normally be seen only by use of a microscope, rather than whether the organism is prokaryotic or eukaryotic.

As used herein, "mixed culture" means a culture or sample containing more than one species, genus, family or category of microorganisms, or some combination of these. Clinical samples, for example, might contain not only a pathogen, but also normal flora and possibly also other organisms which are not part of the normal flora but which are not the causative agent of the patient's most serious illness. "Category," as used herein, is meant to distinguish among the following types of organisms: viruses, bacteria, fungi, and protozoa. The term is also intended to encompass cultures which contain more than one "strain" of a particular species of microorganism, when the practitioner wishes to determine the presence of different strains, or their differences in viability or susceptibility to chemical agents, without having first to segregate them into separate cultures.

In contrast to a mixed culture, a "pure culture" means a culture or sample containing only a single strain of a species of microorganism, when one is investigating the characteristics of strains of a microorganism, or a culture or sample containing only a single species of a microorganism, when one is attempting the determine the identity of a species of microorganism.

"Identify," as used herein, refers to the process of determining the taxonomic classification of a microorganism of interest to a practitioner. Depending on the particular purpose of the practitioner's inquiry, that determination could be at one or more taxonomic levels, such as the family, genus, species, or strain of the microorganism. For example, the practitioner may wish to know if a patient sample contains microorganisms of the genus Staphylococcus, whether those microorganisms are of the species *S. aureus*, and whether the strain of *S. aureus* is of a strain which is resistant to particular antibiotics. "Identity," as used herein, refers to the taxonomic classification resulting from this process, such as identifying the presence of *S. aureus* in a sample.

The term "antibiotic," as used herein, means a chemical agent which has, or which may have, activity in inhibiting the replication of, or of killing, a microorganism of interest. For convenience of reference, the term is used broadly herein to refer to such agents whether the microorganism of interest is a bacterium, virus, fungus, or protozoan. Thus, it includes antibacterial, antiviral, antifungal, and antiprotozoan agents, depending on the category of microorganism of interest to the practitioner. The terms "antibiotic" and "chemical agent" are generally used herein as synonyms.

As used herein, the phrase "culturing the microorganism in an aqueous medium," refers (a) to culturing the microorganisms directly in an aqueous medium for microorganisms, such as bacteria, which can be cultured successfully in this manner, and (b) to culturing the microorganism in cells which are themselves in an aqueous medium for microorganisms which are intracellular parasites. For example, viruses and malarial parasites are typically cultured in cells which are themselves cultured in an aqueous medium.

As used herein, "analog-specific binding member" or "binding member" means a moiety, component, compound, antibody, fragment of an antibody, or other entity which has the property of being able to bind specifically to a nucleic acid analog but which does not bind in any appreciable degree to a natural nucleotide or nucleic acid precursor.

The term "incorporated" when used herein in relation to an analog refers to a nucleoside analog which has been integrated into the cellular (or, in the case of a virus, viral) DNA or RNA by the cell's (or virion's) synthetic machinery.

The terms "grow" or "growth" used herein with respect to a microorganism or a culture of microorganisms refers to replication, that is, to an increase of the number of the microorganisms rather than an increase in the size of a microorganism. The terms "replicate" and "grow" are used generally used synonymously herein except when a different meaning may be required by context.

The word "culture," when used as a noun, refers herein to a population of one or more strains or species of microorganisms, usually in a medium permitting their replication. When used as a verb, "culture" refers herein to a period of time during which the microorganisms are given an opportunity to replicate, if they can under the particular conditions to which they are exposed.

As used herein, "nucleic acid analog," "analog," "nucleoside analog," or "nucleotide analog" means a non-natural variant of a nucleic acid precursor, such as one of the four deoxyribo nucleosides—deoxyadenosine, deoxyguanosine, deoxycytidine, and deoxythymidine—which are the natural components of DNA, or one of the four ribonucleosides which are the natural components of RNA. The term "analog" as used in these phrases indicates that DNA polymerase accepts the triphosphate derivative of such a moiety in place of the correct (i.e. with respect to the template nucleoside) triphosphate precursor during DNA synthesis. See, e.g., Stryer, L., Biochemistry 3rd Ed. 1988 (W. H. Freeman and Co., New York); Watson, J., et al., Molecular Biology of the Gene, 4th Ed., 1987 (Benjamin Cummings, Menlo Park, Calif.).

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term "antibody" also includes antigen binding forms of antibodies (e.g., Fab, F(ab)$_2$).

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, for example, as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (See, e.g., *Fundamental Immunology* (Paul, ed., 3d ed. 1993). While various antibody fragments are defined in terms of the digestion of an intact antibody, one of skill will appreciate that such fragments may be synthesized de novo either chemically or by utilizing recombinant DNA methodology. Thus, the term "antibody", as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "immunoassay" is an assay that uses an antibody to specifically bind an analyte. The immunoassay is characterized by the use of specific binding properties of a particular antibody to isolate, target, and/or quantify the analyte.

The phrases "specifically (or selectively) binds to an antibody," "specifically (or selectively) immunoreactive with," and "specifically recognizes (or recognized by)" when referring to a nucleotide analog, refer to a binding reaction that is determinative of the presence of the nucleotide analog in a heterogeneous population of nucleic acids and other biologics. Thus, under designated immunoassay conditions, the specified antibodies bind to a particular nucleotide analog and do not bind in a significant amount to natural nucleotides present in the sample. A variety of immunoassay formats ay be used to select antibodies specifically immunoreactive with a particular nucleotide analog. For example, solid-phase ELISA immunoassays are routinely used to select antibodies specifically immunoreactive with a protein (see, e.g., Harlow & Lane, *Antibodies, A Laboratory Manual*, 1988 (Cold Spring Harbor Laboratory, Cold Spring Harbor, N.Y.), for a description of immunoassay formats and conditions that can be used to determine specific immunoreactivity), and can be used in like manner to select those specifically immunoreactive with a nucleotide analog. Typically a specific or selective reaction will be at least twice background signal or noise and more typically more than 10 to 100 times background.

The terms "capture" or "capturing" used in connection with a nucleic acid incorporating a nucleic acid analog, mean that the nucleic acid has been recognized by and bound to an analog-specific binding member. Often, the analog-specific binding member will itself be bound to a solid support, such as a bead or other surface.

These terms are also used herein in several secondary senses. In certain uses, for example, it may be convenient to add the analog-specific binding member, such as a monoclonal antibody, to a solution containing nucleic acids which may have incorporated nucleic acid analogs. The binding member is then allowed to complex with any nucleic acids in the solution which have incorporated a nucleic acid analog, following which the complex can be isolated by, for example, contacting the complexes with surfaces coated with a substance, such as protein A, which binds the Fe portion of antibodies, or with antibodies which will recognize the binding member. This process of binding complexes of nucleic acids incorporating nucleotide analogs and analog-specific binding members is also referred to herein as "capture" or "capturing." Finally, "capture probes" are nucleic acid sequences used to hybridize to a target sequence where what is desired is not the amplification of a sequence flanking the target sequence (as is intended when a PCR primer is used), but rather information on whether the target sequence itself is present. Typically, the capture probes are selected to hybridize to sequences which provide specific identification of the organism of interest.

Which of the particular meanings of "capture" or "capturing" is intended will be clear in context.

III. USES OF THE INVENTION

A. Introduction

The invention is expected to be useful in the identification of microorganisms, in clinical, research, industrial, and public health applications.

B. Clinical Uses

1) General

The invention is expected to be useful in clinical microbiology. In this regard, the invention is expected to be useful in aiding the diagnosis of bacterial, viral, fungal and protozoan diseases affecting particular patients and especially useful in the determination of which chemical agents are effective against the particular organism or strain of organism infecting a particular patient.

2) Bacterial Identification

The invention can be used in connection with any bacterium, pathogenic or non-pathogenic, so long as the bacterium can be cultured in a manner permitting uptake of nucleic acid analogs. Use of the invention is expected to be useful, for example in the rapid identification of antibiotic resistant strains of organisms such as *Staphylococcus aureus* and *Mycobacterium tuberculosis*, and may optionally be used to determine to which antibiotics or combinations of antibiotics the particular strain of bacterium infecting the patient is susceptible. Additionally, the invention should be useful in distinguishing between diseases with similar clinical manifestations but different causative agents, with possible differences in the preferred course of treatment.

3) Fungal Identification

The invention is also expected to be useful in the identification of pathogenic and non-pathogenic fungi, as well as determining which agents are effective against the fungi infecting patients. Fungi cause both opportunistic and primary infections ("mycoses") in humans ("primary" pathogens are those capable of establishing infection in a normal host). See generally, T. J. Walsh and D. D. Dixon, Spectrum of Mycoses, in S. Baron et al., eds., *Medical Microbiology*, 3rd Ed. 1991 (Churchill Livingstone, N.Y.) (hereafter "Baron;" the entirety of Baron is hereby incorporated by reference). Both the systemic, "deep" disease due to such primary pathogens as *Histoplasma capsulatum* and the opportunistic mycoses caused by *Candida albicans* or *Cryptococcus neoformans* can be life threatening. The invention is expected to be helpful in diagnosing, and in determining appropriate treatment for, these and other fugal infections.

4) Parasitic Infections

The invention is also expected to be useful with regard to parasitic infections. Infections caused by the unicellular protozoa and the multicellular helminths number in the billions annually and cause a wide range of diseases. The invention should be useful in the diagnosis of at least some of the protozoan parasites, and especially those, such as *N. fowleri*, which require culturing for definitive diagnosis. It should also prove broadly useful in the determination of appropriate treatment of an infection by any parasite which can be cultured in a manner which permits the uptake of nucleotide analogs and the lysing of cells to expose nucleic acids incorporating such analogs to capture by binding members, as further described herein. For example, in some geographic areas, *Plasmodium falciparum*, the organism associated with the majority of the one to two million deaths annually from malaria, has developed resistance to chloroquine, the first-line agent used in treatment. The invention should be useful in determining to which agents the parasites infecting an individual show susceptibility.

5) Viral Infections

The invention should be useful in the diagnosis of viral diseases, as well as the determination of agents to which particular viruses show susceptibility. In this regard, the invention is expected to be useful in the diagnosis or confirmation of infection by any virus which can be cultured in a manner which permits incorporation of nucleotide analogs. Exemplary viruses which can be grown in culture include lentiviruses, such as HIV, flaviviruses, such as dengue virus and yellow fever virus, respiratory syncytial virus, a serious pathogen affecting infants, and the human herpesviruses, including herpes simplex viruses 1 and 2 (HSV), Epstein-Barr virus (EBV), varicella zoster virus (VZV), the causative agent of shingles and chickenpox, and cytomegalovirus.

C. Screening of New Chemical Agents

As noted above, the invention may be used to determine the susceptibility of the particular strain of an organism infecting a patient to chemical agents. But the invention also has important applications in screening novel chemical compositions and chemical compositions not previously employed as antibiotics for their potential efficacy as agents to kill or inhibit the growth of microorganisms. This use is expected to be of considerable value to pharmaceutical companies and public health agencies in the effort to develop new agents faster than pathogens can develop resistance to those already in use.

In general, the invention can be used for such screening purposes with respect to any organism which can be cultured in a manner which permits the incorporation of nucleotide analogs, which can be subsequently lysed to capture nucleic acids incorporating the nucleotide analogs, and for which sufficient sequence information s available to permit the design of appropriate primers. Although the invention can be practiced by sequentially repeating the steps, once in the presence of the antibiotic and once without, screening will more typically involve dividing cultures of the organism into multiple aliquots. The chemical compositions of interest (the agents being tested) are then introduced into a first group of the aliquots, while a second aliquot is reserved as a control to which no agent is added. The relative amounts of the nucleotide analogs incorporated in each aliquot of the first, test, group are then compared to the amounts incorporated in the organisms grown in the presence of the agents in the second, control group so that the relative effectiveness of the agents being tested can be determined. If desired, the assay can also be run with a further aliquot to which one or more current agents thought to be effective against the organism in question are added to compare the effect of the new agent against those currently known. And, for those organisms for which reasonably large quantities can be cultured, large numbers of aliquots can be cultured and tested in parallel, permitting the testing of large numbers of potential agents to be tested at once. This capability is expected to improve the efficiency and to reduce the cost of such testing.

D. Uses in Detecting the Presence of Viable Organisms

The invention is expected to have important uses in the detection of whether viable pathogens are present. One such use is the detection of the identity of any viable bacteria in processed foods, and particularly in ground beef and other meats. The ability to rapidly confirm or disprove the presence of significant contamination may for example reduce or eliminate the need for destruction or recall of ground meats or other foods in cases where contamination was possible but not certain by demonstrating that the meats or other foods in question are not contaminated with viable bacteria at the time of testing. The invention should also prove useful in food processing plants, hospitals, laboratories, and other facilities to determine whether surfaces are free of pathogens or whether additional or more stringent sterilization or containment procedures are required.

E. Public Health Monitoring

As indicated earlier, the presence of coliforms, such as *E. coli*, in waters off beaches is often used as a marker for the presence of untreated sewage. The invention should be useful in the regular testing of water samples to determine whether coliforms are present, and whether, if previously found to be present, the organisms are now absent, without first having to isolate the various microorganisms in the sample.

In another application, the invention can also be used to determine the presence of Cryptosporidium in water supplies. The importance of testing municipal water supplies for the presence of this organism, which can be life-threatening to those with immunocompromised immune systems, was underscored in 1993 by the contamination of the Milwaukee water system and the resulting need for hundreds of thousands of residents to boil their drinking water until the infestation was controlled. The invention will also permit testing of municipal water supplies and other waters for the presence of other pathogens. While cholera is fortunately not often a public health problem in the U.S., the invention can be used for detecting the presence of *Vibrio cholerae*, the causative agent of cholera, in water supplies without first having to isolate it from the various other microorganisms which might also be present in the sample.

IV. ASSAY FORMATS

The choice of the particular assay format is not critical to the invention; rather it will depend on the convenience of the user. In its broadest use, assays according to the invention can be used to determine the viability of organisms in a sample. In other embodiments, assays can be used to test the susceptibility of microorganisms in a sample to known chemical agents, or to determine whether a possible new chemical agent has inhibitory or growth-stopping effects on a particular organism, such as a pathogen.

The general format of an assay can be described by specific reference to the determination of the susceptibility of microorganisms to chemical agents. For ease of description, the microorganisms will be assumed to be bacteria, although fungi, protozoa and viruses can be employed with modifications familiar to persons of skill in the art. (For example, viruses are intracelluar parasites and will therefore typically be grown in cell culture rather than in an aqueous medium. Further, individual viruses are known as virions rather than as cells. Similar adjustments are necessary in referring to fungi and protozoa. Persons of skill in the art are familiar with these distinctions and will easily adapt the following description for use with the respective category of organism.)

First, a population of microorganisms is divided into at least two subpopulations (if one is seeking to determine only if the microorganism is viable and not its sensitivity to an agent, the population need not be divided). The subpopulations are then cultured in the presence of a growth-supporting medium and a labeled nucleoside analog which can be incorporated into the nucleic acid of cells synthesizing such acids, and which permits capture by the analog of nucleic acids containing the analog. An antibiotic, potential antibiotic or chemical agent (hereafter collectively referred to as "agent") is then added to the medium of at least one of the subpopulations and at least one of the subpopulations is left free of the agent. The microorganisms are then lysed to expose the nucleic acids, the labeled nucleic acids are captured by a ligand or other agent which can recognize the labeled nucleotide analog, the captured nucleic acids are separated from those which were not captured, typically by eluting or washing off the nucleic acids which were not captured, the separated, captured nucleic acids are selectively amplified, and the levels of the nucleic acids from microorganisms grown in the presence of the agent or potential agent are compared to those from microorganisms grown in the absence of the agent.

The present invention is based upon the concept that replication of a microorganism is preceded by the synthesis of its DNA (or RNA, in the case of an RNA virus). Therefore, one sensitive and rapid measure of the effect of a specific chemical on the growth of a microorganism is the effect of that chemical on the synthesis of DNA (or, in the case of an RNA virus, RNA) by the microorganism. Thus, if a chemical is an inhibitor, i.e., it inhibits or prevents growth of the microorganism, its effect is manifested by inhibition or prevention of synthesis of DNA (or RNA). Conversely, if a chemical supports or stimulates growth of the microorganism, its effect is manifested by maintained or increased DNA (or RNA) synthesis.

When employed for this purpose, a specimen to be subjected to analysis, for example blood, urine, a mouth or vaginal swab, or a sample of food or of water believed to contain bacteria or protozoa, is obtained. If not already in the form of an aqueous suspension, the specimen is usually suspended in an aqueous medium prior to being subjected to the process of this invention. The size of the sample is not critical, provided a sufficient number of microorganisms are obtained to permit the intended procedures to be performed. Further, the number of bacteria present in the aqueous suspension are not narrowly critical, provided a sufficient number of bacteria are present for the procedure of this invention to detect differences between test and control samples. The time required to perform the analysis, however, can be reduced as the concentration of microorganisms increases. If the specimen has too low a cell concentration, it may be concentrated by known techniques, such as centrifugation or by culturing.

In the Examples, below, the organisms were typically grown in overnight cultures to permit use of saturated cultures. Under some circumstances, however, such as the determination of which antibiotics to use in a seriously ill patient, time may not permit overnight culturing, in which case the sample would likely be briefly cultured and then used.

The aqueous bacterial suspension which is to be subjected to the analytical technique of this invention desirably includes nutrients capable of supporting bacterial growth. Consequently, the bacteria are desirably suspended in liquid culture media, in particular culture media which are known as "complete" culture media. Such liquid culture media are well known in the art.

The first step of the process of this invention comprises adding one portion of the sample to a complete liquid culture medium containing the chemical whose activity is to be determined, and adding another portion of the sample to the culture medium without the chemical to serve as a control. The culture medium will usually be the same as that used in preparing the initial sample. The size of the resulting mixtures is not highly critical, provided there is sufficient material in the test and control media to permit one to obtain detectable growth. On the other hand, it is desirable to minimize the size of the sample to conserve materials. In general, analytical samples having a volume in the range of from about 250 microliters up to about 1 to 2 milliliters are useful. In forming such a sample, the bacterial suspension is preferably added to the culture medium contained in a suitable container, thereby diluting the bacterial suspension by a factor of about 10 to 100. For example, a 100 $\mu$l sample of bacteria suspension is diluted with about 1 ml of liquid culture medium to make up the analytical specimen.

The test sample also contains the chemical whose activity is to be determined. The chemical may be a known antibiotic when the test is employed to ascertain susceptibility of the bacteria to antibiotics, or it may be an experimental chemical whose antibacterial activity may be under investigation. The chemical may also be one capable of stimulating bacterial growth, in which case that effect will be detected by the incorporation of more nucleotide analog in the test sample than in the control sample.

After the test and control specimens are formed, they are incubated under conditions suitable for sustaining bacterial growth. The period of incubation is that period sufficient to obtain detectable growth, which will differ depending upon factors such as bacterial species and concentration of organisms in the sample. Different organisms have different rates of growth. Further, differences in growth rates between test and control specimens are more readily determined if high cell concentrations or high concentrations of nucleotide analog are present in the samples. In general, however, the incubation should be at least about one-half hour. To be of the most value in rapid clinical determination of antibiotic susceptibility of bacteria, the conditions should be such that the incubation period is as short as possible. In the Examples; the microorganisms were grown to early log phase, about one and a half hours. For very slow growing bacteria, such as *M. tuberculosis*, however, a period of days or longer may be necessary. Example 6 shows that an exemplary member of the *M. tuberculosis* complex could be detected after incubation with BrdU for two days. Periods of culturing required to detect any particular organism can be readily determined by a simple time course assay, in which the nucleoside analog of choice, for example BrdU, is added to a culture of the organism and samples taken at designated intervals. And, regardless of organism, if rapid determinations are not necessary for the purpose of the assay, longer incubation periods can of course be used.

After incubation of the test and control specimens for a period of time, the nucleotide analog is added to both specimens and the resulting samples are then incubated for an additional period of time. In the Examples below, the samples were typically incubated for an additional hour. As is noted above, the bacteria in both samples will incorporate the nucleotide analog into newly synthesized DNA, and the differences in the rates of bacterial uptake of the analog in the control and test specimens is a measure of the effect of the test chemical on bacterial growth. That is, a slower rate of uptake by bacteria in the test specimen, as compared to the control, results if the chemical is an effective antibiotic. Conversely, increased analog uptake in the test specimen results if the chemical stimulates bacterial growth.

It is useful if the time of addition of the analog is chosen to maximize the differences detectable between the test and control specimens. Accordingly, the addition of the analog is typically delayed for some time after the agent is added. If the analog is added early in the cycle, at a point in time before the test agent has had a significant effect on the test bacteria, i.e., before there has been an opportunity for significant differences in the sizes of the respective bacterial populations to occur, the measurement of differences will be more difficult. On the other hand, there must be a sufficient time period after addition of the analog to allow a measurable difference in analog uptake to occur. As a general rule, the incubation period following addition of analog should be at least in the range of from about 5 minutes to about 1 hour. Of course, more time can be permitted, especially in the case of slow growing organisms where rates of uptake can be expected to be low. In the Examples, below, typically 1 hour was permitted for analog incorporation.

Following incubation in the presence of analog, the microorganisms are lysed to expose their nucleic acids and the nucleic acids labeled with analog are captured and selectively amplified, after which they are analyzed to determine the respective analog uptake of the microorganisms. Typically, the amplification products will be hybridized with probes. In most cases, the probes will be DNA. The DNA used as a probe can be selected to be of a sequence specific for a particular organism, or can be selected to hybridize to a sequence common to many organisms in a group. Design of such probes is known in the art and is discussed in more detail under Amplification Methods, below. Typically, the probes are labeled in a manner permitting their recognition by a second antibody, which can then serve as a substrate for a chromogenic, fluorogenic, or other reaction. For example, the probes can be labeled with digoxigenin using the 3'DIG Oligonucleotide Labeling Kit (Boehringer Mannheim, Germany). The sample is then incubated with alkaline phosphatase- or horseradish peroxidase-conjugated anti-digoxigenin antibodies, and then incubated with a substrate appropriate for the label, such as p-nitrophenyl phosphate for an alkaline phosphatase conjugated antibody, or tetramethylbenzidine (TMB) for peroxidase. Absorbance is then read at the appropriate wavelength on a multiplate reader. One method for making such determinations is set forth in the Examples below, but others known in the art can also be used.

V. CULTURING METHODS

To practice this invention, one has to culture one or more microorganisms present in a sample. There are a variety of ways of culturing microorganisms, and a comprehensive literature exists on the subject, covering the temperature ranges, nutritional needs, pH tolerances, oxygen requirements, and other growth parameters for most organisms within each of these groups. See, e.g., Baron, supra; Prescott, L., et al., *Microbiology*, 1990 (Wm. C. Brown, Dubuque, IA); Zuckerman, A., et al., eds., *Clinical Virology*, 3rd Ed. 1994 (John Wiley & Sons Ltd., Chichester, U.K.); White, D. and Fenner, F., *Medical Virology*, 4th Ed., 1994 (Academic Press, San Diego, Calif.); Freshney, R., *Culture of Animal Cells*, 3rd Ed., 1994 (Wiley-Liss, New York); and Fraenkel-Conrat, H. and Wagner, R. R. (eds.), *Comprehensive Virology*, Plenum Press, New York (1979), all of which are incorporated by reference. The choice of a particular method of culturing the microorganism or microorganisms of interest is not part of the current invention; it is only necessary that the culture method permits the microorganism to take up nucleotide analogs from the culture medium and incorporate them into its nucleic acids.

A brief survey of culturing needs may be illustrative. Many bacterial pathogens and commensals, as well as other pathogenic or commensal organisms, show optimal growth at conditions approximating those of the sites at which they are usually found within the body. For example, *Staphylococcus aureus* grows optimally at 30–37° C.; *E. coli* at 37° C., *Neisseria gonorrhoeae* at 35–36° C., and the protozoa *N. fowleri* and *T vaginalis*, at 35° C. and 32–39° C., respectively. With respect to pH, *S. aureus* grows optimally at pH 7–7.5, *E. coli* grows best at pH 6–7, and various Lactobacillus species that colonize the female genitourinary tract maintain the vagina at a pH of 4–4.6. Bacteroides, *S. epidermidis*, Enterococci, and others are able to grow at this low pH.

Oxygen requirements for culturing vary widely. For example, Streptococcus faecalis, an aerotolerant anaerobe, grows equally well in the presence or absence of oxygen, whereas Clostridium and Bacteriodes are obligate anaerobes which die in its presence. Oxygen requirements for culturing microorganisms are well known in the art.

Nutritional needs have also been studied. *S. faecalis*, for example, requires eight vitamins, such as folic acid, for growth, and in fact can be used to assay the vitamin content of a substance by growing the organism in a medium containing ample amounts of all of its vitamin requirements but the one to be assayed, and adding the substance to be assayed.

Viruses generally need to be cultured in plant or animal cells appropriate for the virus of interest ("permissive" cells). An exemplar protocol for viral preparation and assay is taught at pp. 402–403 in Freshney, supra, for use with HSV. Freshney further notes that, while HSV replicates in a number of human and animal cell types, other viruses require specific cell types. For example, he notes that CMV replicates only in human fibroblast cells while Bunyaviridae replicate in amphibian cell lines and polyoma virus in mouse embryo cells. Cell types required for culturing other viruses are set forth in Baron, supra, and White and Fenner, supra.

Because of their diversity, protozoa diverge in their culture needs. For example, malarial parasites can be grown in cell culture, while the free-living amoebas *N. fowleri*, and Acanthamoeba, both of which can cause encephalitis, can be grown in warm fresh water.

VI. NUCLEOTIDE ANALOGS AND BINDING MEMBERS

The invention requires that microorganisms be cultured in the presence of nucleotide analogs. Preferably, the nucleoside analogs used with the invention are those which are non-toxic when incorporated into cellular DNA or RNA in detectable amounts. In particular, halodeoxyuridines are the preferred analogs of thymidine. More preferably, 5-chloro-, 5-bromo-, or 5-iododeoxyuridine are used as analogs of thymidine. And most preferably, 5-bromo-2'-deoxyuridine ("bromo-deoxyuridine" or "BrdU") is used as an analog of thymidine.

The following nucleic acid analogs, which are known to incorporate into RNA (those listed on the left side of each pair below) or DNA (those listed on the right side of each pair below) are also preferred for use in the invention:

6-azauridine and 6-aza-2'-deoxyuridine 3-deazauridine and 3-deaza-2'deoxyuridine 5-azacytidine and 5-aza-2'-deoxycytidine 8-azaguanine and 8-aza-2'-deoxyguanosine 6-thioguanine and 6-thio-2'deoxyguanosine 6-mercaptopurine and 6-mercaptopurine-2'-deoxyriboside 4-thiouridine and 4-mercapto-2'-deoxyuridine.

In the case of thio- and mercapto- nucleotide analogs, a preferred embodiment for the binding member is a thio-specific reagent, such as immobilized para-chloromercuribenzoate (PCMB). In a preferred embodiment for any of the nucleotide analogs, such as a halodeoxyuridine, the binding member is an antibody which recognizes that particular nucleotide analog. In a particularly preferred embodiment, the binding member is an antibody recognizing BrdU. In the most preferred embodiment, the antibody is a monoclonal antibody recognizing BrdU.

VII. LYSING METHODS

A number of techniques are known in the art for lysing cells of different microorganisms and for lysing virions to obtain their nucleic acids. In general, any lysing method appropriate for the target microorganism can be used in connection with the invention, so long as the lysate is then made compatible with the media used for the capture step, either before adding it to the capture media or by the media itself. For example, if the cells are lysed by NaOH, the NaOH should be neutralized by the addition of a suitable amount of acid or of buffering media, or the capture media should have sufficient buffering capacity for the amount of lysate used in connection with the capture step. The Examples, below, set forth examples of the use of NaOH for lysis, followed by the use of a buffered medium in the capture step.

Bacteria are usually harvested by centrifugation and can be lysed by one of a number of means, including boiling, sonication, alkali lysis, exposure to organic solvents, exposure to ionic or nonionic detergents, or exposure to lytic enzymes, such as lysozyme or protease K. An exemplar procedure is set forth in Atlas, R. and Bej, A., Detecting Bacterial Pathogens in Environmental Water Samples By Using PCR and Gene Probes, in Innis, M., et al., eds., *PCR Protocols* 1990 (Academic Press, San Diego Calif.) (hereafter "Innis"; the entirety of Innis is hereby incorporated by reference). The Examples below detail two of the protocols used in the studies reported therein.

An exemplar method for lysing fungi starts by first grinding the fungi in a mortar and pestle in liquid nitrogen. Lee, S. and Taylor, J., Isolation of DNA from Fungal Mycelia and Single Spores, in Innis, supra. The protocol further teaches the extraction of DNA from the fungi for PCR or other procedures.

Protozoa can be lysed by, for example, boiling them in water. The cells are first pelleted and washed in phosphate-buffered saline (PBS), resuspended in PBS, and incubated in a heating block at 95° C. or boiled for 3–5 minutes. Saiki, R., Amplification of Genomic DNA, in Innis, supra. If PCR is to be used for amplification, the cellular debris can be pelleted by centrifugation.

Viruses can be collected from tissue culture supernatants or in the blood by first centrifuging the supernatant or blood at 500×g for 5 minutes, removing the centrifuged supernatant, and centrifuging it again at 10,000×g for 10 minutes to remove cellular debris. The resulting supernatant is then centrifuged at 50,000 rpm for 45 minutes in a SW 50.1 rotor to pellet the viruses. The viruses can then be prepared for PCR or other procedures by standard methods taught, e.g. by Kawasaki, E., Sample Preparation from Blood, Cells, and Other Fluids, in Innis, supra.

VIII. CAPTURING AND SEPARATION PROCEDURES

A. Antibody Capturing Procedures

One convenient way to capture nucleic acids bearing incorporated nucleotide analogs is to use antibodies which recognize epitopes present on the nucleotide analog but which are not also present on the naturally occurring nucleotides which ordinarily compose DNA and RNA. Both polyclonal antibodies and monoclonal antibodies (MAbs) to nucleotide analogs are known in the art. For example, MAbs to halodeoxyuridines such as BrdU have been known since the early 1980's, see, e.g., Gratzner, Science, 218: 474–475 (1982), and are commercially available. Antibodies to other nucleotide analogs can be made following standard protocols (see, e.g. Harlow & Lane, supra), and tested against a panel of naturally occurring nucleotides to eliminate antibodies which recognize epitopes common to both naturally occurring nucleotides and non-natural nucleotide analogs.

It is expected that commercially available antibodies passing these tests will be suitable for use in the invention. We have found, however, that antibodies available from different suppliers differ in the amount of background binding to unlabeled DNA. Such differences in background could reduce the sensitivity of detection in applications where it is desirable to use relatively large amounts of DNA or to run more PCR cycles (or a like amplification step). For these applications, it is desirable to test the antibodies available from different suppliers (by, for example, running a test on labeled and unlabeled E. coli DNA using each antibody in a series of different dilutions of DNA) to determine which one or ones provide a level of background acceptable for the contemplated use. In our tests, anti-BrdU antibodies supplied by Sigma Chemical Corp. (St. Louis, Mo.) showed the lowest amount of background binding and are therefore preferred.

The antibodies can be used to capture the nucleotide analogs in a variety of ways known in the art. For example, the antibodies can be covalently or otherwise bound to a solid support, such as a bead or a column. A number of methods are known for coupling antibodies to solid supports. For example, protein A binds specifically to the Fc domain of antibodies and, accordingly, antibodies will bind specifically to protein A beads or columns, or to surfaces coated with protein A. Such coating is routinely performed by incubating the surface with diluted protein A, and adding and then removing a blocking solution prior to use.

The bead, column, or other surface can also be activated chemically to contain a reactive group which will bind to an antibody. Commonly used for such activation are carbonyldiimidazole, cyanogen bromide, and glutaraldehyde. Further, the antibody can be activated by, for example, carbodimides, condensing agents, or glutaraldehyde, to place a reactive group on the antibody, which is then exposed to the beads, column, or other solid surface of choice. Alternatively, the antibodies can be biotinylated. Since biotin binds with high affinity to streptavidin or avidin, one can use beads of those materials or use those materials to coat beads, a column, a tube, or another solid surface. See, Harlow and Lane, supra. Columns can also be packed with polyacrylamide, polysaccharide, agarose, or polyacrylic beads, or other beads or materials to which antibodies can be bound and which allow solutions or mixtures containing antigen (nucleotide analogs) to come into contact with bound antibody while permitting the bulk of substances which do not bind to the antibody to pass through the column.

Embodiments in which protein A or other materials are coated onto the sides of tubes require that the DNA diffuse to the walls of the tubes for capture. Thus, assays using beads and other particles, which can provide a larger surface area and reduce the distance over which the DNA must diffuse, should have a higher sensitivity than tube assays. Further, in bead and particle embodiments, the number of the beads or particles can be adjusted to increase the overall capacity of the assay. Use of magnetic beads can render later separation steps more convenient.

Once the antibody of choice is bound to a solid support, an assay can be conducted by exposing the antibody to a lysate of the material to permit any antigen specifically recognized by the antibody to be bound. If the surface to which the antibody is bound is a solid surface, the lysate can simply be poured slowly over the surface. If the antibody is bound to streptavidin beads, then the lysate can be mixed with the beads and gently stirred. Any nucleic acids incorporating the analog recognized by the antibody are captured by binding to the antibody. After an appropriate period has elapsed, the beads are typically washed to separate nucleic acids which have not bound to the antibody from those which have been bound, following which the immune complexes (the antigen bound to antibody) are disrupted by appropriate elution conditions. If the beads or other materials are packed in a column, then the lysate mixture is simply run through the column to permit the formation of immune complexes between the nucleotide analog and the antibody, after which the unbound material is separated by washing the column prior to breaking the immune complexes by appropriate elution conditions.

In the Examples set forth below, in which the immune complexes were bound to protein A coated PCR tubes, the amplification step could be conducted without first eluting the immune complexes. Depending on the method used, however, it may be necessary to elute the complexes before amplification. Appropriate elution conditions for any given antibody-antigen reaction are usually determined empirically (see, e.g., Harlow and Lane, supra, at p. 547). Commonly, the elution reagent is selected from a high pH reagent, such as 100 mM triethylamine, pH 11.5, a low pH reagent, such as 100 mM glycine, pH 2.5, a high salt reagent, such as 5 M LiCl, 10 mM phosphate, pH 7.2, an ionic detergent, such as 1% SDS, a dissociating agent, such as 2 M urea, a chaotropic agent such as 3 M thiocyanate, or an organic solvent, such as 10% dioxane. Appropriate pre-elution washes and collection buffers for these and other reagents of each type are known in the art. See, e.g., Harlow and Lane, supra, at p. 549.

In a preferred embodiment, BrdU labeled analogs were captured by anti-BrdU antibodies and the immune complexes captured by Protein A-coated 0.5 ml microcentrifuge tubes. The tubes were prepared by diluting concentrated stock solution of Protein A to 100 µg/ml with PBS and adding 100 µl to each microcentrifuge tube. The tubes were incubated overnight at 4° C., the Protein A solution removed by pipette, and 250 µl of blocking solution (1% bovine serum albumin (BSA), 0.2 M Tris, pH 7.5, 50 µg/ml single stranded DNA) added for at least 5 minutes but not longer than 1 hour. Tubes so prepared could be used immediately or stored at 4° C.

While protein A has the advantage of direct affinity for the anti-BrdU antibodies, streptavidin was also examined as a coating for containers to demonstrate that other methods known in the art for binding antibodies would work in the invention. Streptavidin has both an extremely high affinity for biotin, and exceptional stability, which could be of value in manufacturing kits or for preparing materials for later use.

Studies were conducted using streptavidin labeled tubes. First, BrdU-labeled DNA was adsorbed with anti-BrdU antibody. Then, a biotinylated secondary antibody with an anti-mouse specificity was added. This step effectively labeled the anti-BrdU antibody with biotin through a secondary antibody "bridge". Finally, the entire complex was adsorbed to the streptavidin labeled tube for immune-affinity capture and PCR. The results indicated that this system worked as efficiently as the protein A system in binding labeled nucleic acids recognized by anti-BrdU antibodies.

Finally, immune complexes can be removed from solution by means known in the art that do not involve binding to surfaces. For example, antibodies can be coupled to magnetic or paramagnetic materials and the complexes separated from other materials in the medium by positioning a magnet on one side and then drawing off the material that does not migrate towards the magnet after a suitable period of time.

B. Non-antibody Based Capture Procedures

Depending on the nucleotide analog employed, nucleic acids incorporating nucleotide analogs can be captured by other means than antibodies. For example, if the nucleotide analogs chosen for use are thio- or mercapto- analogs, they can be captured by para-chloromercuribenzoate (PCMB). The PCMB may be immobilized on a solid support, as such as a bead or column, as described above, washed to remove unbound nucleic acids and other materials in the lysate, and the bond between the analog and the PCMB/analog bond then disrupted by excess thiol reagent, such as cysteine, dithiothreitol (DTT), or mercaptoethanol, to free the bound analog for analysis.

C. Separation Procedures

A number of separation procedures are available and well known in the art. Several means of separating captured nucleic acids from those which have not been captured, elution from columns, washing of beads or other solid surfaces to which the captured nucleic acids have been bound, and magnetic separation, have already been discussed above. Other common methods include precipitation by centrifugation and immune precipitation. The particular method of separation employed is not critical, but should be convenient. Preferred means of separation are set forth in the Examples, below.

IX. AMPLIFICATION OF CAPTURED NUCLEOTIDE ANALOGS

A. Introduction

Once captured, nucleic acids incorporating nucleotide analogs are amplified prior to detection. Nucleic acid amplification methods include, for example, the polymerase chain reaction (PCR), the ligase chain reaction (LCR), e.g. EP 0 320 308, nucleic acid sequence based amplification (NASBA), e.g., EP 0 525 882, transcription mediated replication (TMR) and strand displacement amplification (SDA), e.g., EP 0 623 682.

Probably the most common nucleic acid amplification method in current use is PCR. PCR is a preferred means of amplifying captured nucleic acids since thermal cyclers for performing PCR are already in many labs, the reagents are widely available, and technicians and other hospital and laboratory personnel are already trained in performing it. PCR utilizes a DNA polymerase, primer molecules of opposite sense, and rounds of thermal cycling to cause the exponential replication of nucleic acid molecules; the method is described in, e.g., Mullis, et al., U.S. Pat. No. 4,683,195.

Some of the other amplification methods which can be used in the practice of the invention, including some of those mentioned above, are amplification methods utilizing a catalytic RNA to replicate nucleic acids, U.S. Pat. No. 4,786,600; amplification systems based on strand displacement, see Walker, et al., EP 0 497 272; and different transcription-based amplification methods. Among the latter are those of Malek, WO 91/02818; Kacian, et al., U.S. Pat. No. 5,399,491; Kacian, et al., EP 0 587 266; and McDonough, et al., EP 0 587 298. All of the foregoing are incorporated by reference.

Some of these methods also permit the amplification of RNA. For example, Marshall, U.S. Pat. No. 5,686,272, which is incorporated by reference, discloses the amplification of RNA sequences using LCR. Or, the RNA can be reverse transcribed into DNA and then amplified by LCR, PCR, or other methods. An exemplar protocol for conducting reverse transcription of RNA is taught in U.S. Pat. No. 5,705,365. Amplification of RNA or of DNA reverse transcribed from RNA can be useful in using the invention in connection with detecting the presence of viable viruses with RNA genomes, or with detecting the response of such viruses to current or potential anti-viral agents.

Amplification methods such as the foregoing permit the detection of small numbers of nucleic acid analyte molecules in a sample. For example, by conducting an amplification reaction and then using nucleic acid hybridization with a labeled probe to detect the amplified reaction products (amplicons), the presence of small numbers of a specific nucleic acid in a sample can be determined. This permits the rapid determination of the species of the microorganism in the sample.

B. PCR and design and Selection of Primers

As noted, PCR is a preferred means of amplifying captured nucleic acids for use in the inventive method. The basic methodology and protocols for performing PCR are well known. See, e.g. Innis and Gelfand, Optimization of PCRs, in Innis, supra. PCR involves the use of template DNA and primers chosen to determine if regions of DNA complementary to the primers are present in the template DNA. The choice and design of the primers will vary depending on the purpose of the assay.

General guidelines for selecting efficient and specific primers are known in the art and are taught in, e.g., Saiki, Amplification of Genomic DNA; and Compton, Degenerate Primers for DNA Amplification, both in Innis, et al., supra. At the choice of the practitioner, the primers can be designed to amplify sequences common to a number of organisms, such as all members of a genus, or a sequence specific to a particular species. Id.

If the sample is taken from a patient who may be suffering from one of a variety of infections, the identity of a microorganism in the sample can be rapidly identified by running parallel tests with panels of different primers. If the purpose of the assay is to determine whether a patient is infected by a specific pathogen, such as multi-drug resistant *M. tuberculosis*, then primers specific for that organism may be used so that sequences from the specific pathogen are amplified selectively. Alternatively, degenerate primers can be chosen which will amplify many members of a family of organisms, or primers can be chosen which amplify sequences from a gene common to a group of microorganisms. The identities of the particular microorganisms present can then be determined by any of a number of means known in the art, such as gel electrophoresis, Southern blotting, or the use of capture probes complementary to a portion in the amplified sequence that is specific for an individual species or strain.

The Examples, below, demonstrate such identifications. A set of primers amplifying a gene found in several bacteria were used to amplify nucleic acids from an enteric bacteria, *E. coli*, and two different oral bacteria. The identity of the individual organisms in the culture was then determined using capture probes which hybridize to sequences in the PCR products that are specific to the particular organisms. The specificity with which primers and capture probes hybridize to their complementary sequences permits samples containing multiple microorganisms to be cultured and the various microorganisms identified without the need to first plate out the specimen to obtain pure cultures of the individual microorganisms.

Primers suitable for amplifying sequences of a large number of organisms are known. For example, generic and specific sequences for identifying human papillomaviruses, enteroviruses, hepatitis B virus, HIV, HTLVs, and CMV, are set forth in chapters 39 to 44 of Innis, et al., supra. For those organisms for which suitable primers have not been published, primers can be chosen from sequenced portions of the organism's genome. The relatively few organisms for which insufficient sequence information is currently available to permit design of specific primers can be used in the method of the invention as sufficient sequence information becomes available.

C. LCR

LCR is another method of amplifying captured nucleic acids incorporating nucleotide analogs. LCR is performed by repeated cycles of heat denaturation of a DNA template containing the target sequence, annealing a first set of two adjacent oligonucleotide probes to the target DNA sequence in a unique manner, and a second set of complementary oligonucleotide probes that hybridize to the sequence opposite to the target DNA sequence. Thereafter, a thermostable DNA ligase will covalently link each pair of adjacent probes provided there is complete complementarity at the junction of the two adjacent probes. Because the oligonucleotide products from one round may serve as substrates during the next round, the signal is amplified exponentially, as in PCR. LCR has been extensively described by Landegren et al., Science, 241:1077–1080 (1988); Wu et al., Genomics, 4:560–569 (1989); Barany, in PCR Methods and Applications, 1:5–16 (1991); and Barany, Proc. Natl. Acad. Sci. USA, 88:189–193 (1991), all of which are incorporated by reference. Exemplary protocols teaching the use of LCR is taught in these references and, in conjunction with a novel ligase, in U.S. Pat. No. 5,700,672, which is also incorporated by reference.

X. DETECTION OF AMPLIFIED NUCLEIC ACIDS

A. General

Once amplified, the amplified nucleic acids can be detected, at the practitioner's preference, by any of a variety of means known in the art. Using PCR as an example, PCR products may be detected by the use of labeled nucleotide primers or, alternatively, by detecting the hybridization of product sequences to an appropriately labeled probe.

B. Labeling of Probes and Primers

Typically, primers are labeled at the 5' terminus with biotin or with any of a number of fluorescent dyes. Probes are usually labeled with an enzyme, such as horseradish peroxidase (HRP) and alkaline phosphatase, see, Levenson and Chang, Nonisotopically Labeled Probes and Primers in Innis, supra, but can also be labeled with, for example, biotin-psoralen. See, e.g., Helmuth, Nonisotopic Detection of PCR Products, in Innis, supra. Detailed example protocols for labeling primers and for synthesizing enzyme-labeled probes are taught by Levenson and Chang, supra. Helmuth, supra, teaches a protocol for detecting the presence of PCR products hybridized to probes labeled with HRP or with biotin-psoralen. The protocol instructs the practitioner both on how to determine the hybridization conditions appropriate for the oligonucleotide probe employed, and on how to adjust the conditions, including the stringency, to those appropriate for use of that probe. Or, the probes can also be labeled with radioactive isotopes. An exemplary protocol for synthesizing radioactively labeled DNA and RNA probes is set forth in Sambrook et al., *Molecular Cloning, A Laboratory Manual* 2nd Ed. 1989 (Cold Spring Harbor Laboratory Press, Cold Spring Harbor, N.Y.), which is hereby incorporated by reference. Usually, $^{32}P$ is used for labeling DNA and RNA probes.

C. Exemplary Protocols for Detection of PCR Products

A number of methods for detection of PCR products are known. See, e.g., Helmuth, supra, which sets forth a detailed protocol for detecting PCR products using non-isotopically labeled probes. Generally, there is a step permitting hybridization of the probe and the PCR product, following which there are one or more development steps to permit detection.

For example, if a biotinylated psoralen probe is used, the hybridized probe is incubated with streptavidin HRP conjugate and then incubated then incubated with a chromogen, such as tetramethylbenzidine (TMB). Alternatively, if the practitioner has chosen to employ a radioactively labeled probe, PCR products to which the probe has hybridized can be detected by autoradiography. As another example, biotinylated dUTP (Bethesda Research Laboratories, MD) can be used during amplification. The labeled PCR products can then be run on an agarose gel, Southern transferred to a nylon filter, and detected by, for example, a streptavidin/alkaline phosphatase detection system. A protocol for detecting incorporated biotinylated dUTP is set forth, e.g., in Lo et al., Incorporation of Biotinylated dUTP, in Innis, supra. Finally, the PCR products can be run on agarose gels and nucleic acids detected by a dye, such as ethidium bromide, which specifically recognizes nucleic acids.

XI. KITS

The present invention can be practiced conveniently by using kits. The kits may contain, at the option of the provider, the components for practicing the invention. The kits may contain, for example, one or more containers, such as culture dishes, microcentrifuge tubes or ELISA plates. Containers intended for binding immune complexes of nucleic acids incorporating analogs and anti-analog antibodies may be pre-coated with protein A, streptavidin, or another material permitting ready binding of immune complexes. For example, if biotinylated antibodies are to be used, the containers may be precoated with streptavidin. Additionally, the kits contain primers for identifying the presence of a selected group of microorganisms, such as Staphylococcus species, or of a specific species, such as *S. aureus*. The kits may also contain one or more reagents for use in the invention, such as reagents for performing amplification steps. Preferably, the kits contain instructions for practicing the invention either as an insert or on a label on the package or on items within the packaging.

EXAMPLES

The following examples are provided by way of illustration only and not by way of limitation. Those of skill in the art will readily recognize a variety of noncritical parameters that could be changed or modified to yield essentially similar results.

Example 1

This example demonstrates incorporation of BrdU by *E. coli* and the ability to detect nucleic acids labeled with BrdU. For the convenience of the reader, a schematic representation of the procedure is set forth in FIG. 1.

A Procedure and Results.

*E. coli* cells (ATCC number 33694, more commonly referred to in the literature, and hereafter, as strain HB 101) were grown in L-Broth (Luria Broth: 10 g Bacto-Tryptone (Difco, Ann Arbor, Mich.), 5 g yeast extract, 5 g NaCl per liter). From a saturated overnight culture, 0.04 ml of cells were added to 4 ml of fresh L-Broth. Cells were shaken for about 90 minutes at 37° C. until they entered early log phase (this is usually 1 to 1.5 hours for *E. coli*). Then, 0.04 ml of 100 mM BrdU was added and the cells were grown until the culture reached saturation, as determined by turbidity.

DNA purification was carried out as follows (this protocol is referred to in the examples following as the chemical disruption method). Cells were spun in a microfuge from 2 ml of culture. They were resuspended in 100 μl of TEN (50 mM TrisHCl, pH 7.5, 50 mM EDTA, 100 mM NaCl, in distilled water). A mixture of 100 μl TEN and 5 mg/ml lysozyme was added and the resulting mixture was incubated at room temperature for 5 minutes, at which point, a further 200 μl TEN and 2% SDS was added. The suspension was clear and turned very viscous. At this point, 0.1 vol. 3M sodium acetate, pH 5.5, and an equal volume of phenol/chloroform was added, and mixed, gently but thoroughly, to get an even suspension. The mixture was then spun at 13,000×g for at least 2 minutes. The upper aqueous phase was withdrawn and 2.5 vol. EtOH added to it and mixed well. The DNA formed a stringy precipitate. The DNA was spun 2 minutes at 13,000×g to pellet the DNA, the pellet was dried by adding 0.5 ml 100% EtOH, spinning for 2 minutes at 13,000×g, decanting, and air drying, and then resuspended in 100 μl or more of water. The concentration of the DNA was adjusted spectrophotometrically (1O.D.=50 μg/ml) to 500 μg/ml prior to use.

2 μl of DNA (diluted to 10 μl with water) was denatured by heating in a boiling water bath for 2 minutes. The DNA was immediately added to a tube containing 100 μl of anti-BrdU antibody (Boehringer Mannheim) diluted 1:200 in 1% BSA. The mixture was incubated at room temperature for 1 hour. This mixture was then added to tubes which had been coated with protein A and incubated for a further 15 minutes to 1 hour. The antibody/DNA mix was drawn off with a pipette and a 500 μl aliquot of wash buffer (0.1M Tris pH 7.5, 0.1% Tween) added, after which the tube was inverted and the buffer poured off. This wash step was repeated once. Following the two washes with wash buffer, the tube was washed twice in the same manner with 500 μl aliquots of PBS. Any remaining buffer was then drawn off with a pipetor.

A PCR master mix was prepared containing 20 mM Tris-HCl (pH 8.4), 50 mM KCl, 2 mM MgCl$_2$, 200 AM of each dNTP, 1 μM of each primer (primer selection is discussed in section B of this Example, below), and 1 unit Taq Polymerase (Life Technologies) in a total volume of 100 μl. After washing the tubes, 100 μl of master mix was added. The mixture was overlayered with mineral oil and placed in a Perkin Elmer Cetus thermo cycler. The program used was 1 min. at 94° C., 1 min at 40° C., and 1 min at 72° C. for 35 cycles, followed by a 5 min extension at 72° C., and a 4° C. soak. Seven and a half μl of each sample was then run on a 1.5% agarose gel in TAE (40 mM Tris acetate, pH 8.3, 1 mM EDTA).

Figure 2:
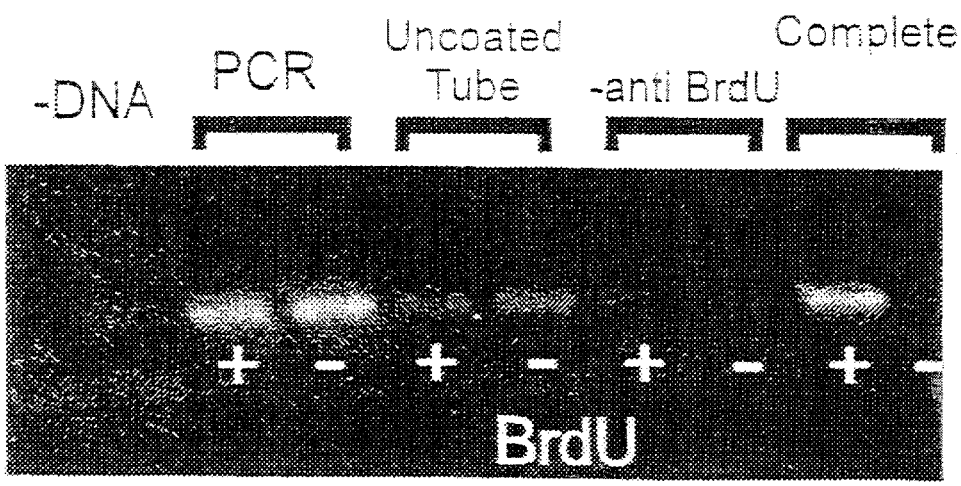
FIG. 2 is a photograph showing the results of an immunocapture assay demonstrating the ability to detect nucleic acids with incorporated nucleotide analog, in this case, BrdU incorporated in DNA of E. coli. The first lane of FIG. 2 (marked "−DNA") is a negative background control containing no DNA. The next eight lanes are PCR reactions run either with DNA labeled with BrdU (denoted "+" in the figure) or DNA that was not labeled with BrdU (denoted "−"). In the first two of these eight lanes, PCR was run on both BrdU-labeled ("+") DNA and on DNA not labeled with BrdU ("−"). In the next two lanes, denoted "uncoated tube," the immunocapture was conducted in containers which were not coated with protein A. Only some very light background was obtained. The next two lanes, marked "-anti BrdU," are immunocaptures without the addition of the anti-BrdU antibodies. Again, little or no signal was obtained. The lanes marked "Complete" denote the use of PCR on labeled DNA, the use of protein A coated tubes, and the use of anti-BrdU antibodies.

The results are shown in FIG. 2. The first lane of FIG. 2 is a negative background control containing no DNA. The next two lanes (denoted "PCR") are PCR reactions run either with DNA labeled with BrdU (denoted "+"in the figure) or DNA that was not labeled with BrdU (denoted "–"). The result shows that BrdU-labeled DNA amplifies as efficiently as non-labeled DNA. In the next two lanes, the immunocapture was conducted in containers which were not coated with protein A. Only some very light background was obtained, indicating that, as expected, some means of retaining the immune complexes is desirable when conducting the assay with antibodies. The next two lanes are immunocaptures without the addition of the anti-BrdU. Again, little or no signal was obtained, showing that, as expected, some means of capturing the labeled nucleic acids is desirable. In the lanes marked "Complete" (denoting the use of PCR on labeled DNA, the use of protein A coated tubes, and the use of anti-BrdU), a strong band of the correct size is obtained from DNA that was labeled with BrdU, but not from DNA which was not labeled. This study demonstrated the ability of the immunocapture/PCR system to differentiate between cells grown in the presence and absence of BrdU.

B. Design of Primers and Probes Used in These Studies

For these studies, the general strategy was to design one set of primers which could yield products from a number of bacterial species, including both *E. coli* and oral bacteria. *E. coli* was preferred for studies showing the efficacy of the system in part because no special handling is necessary. Oral bacteria were chosen in part to demonstrate that the results demonstrated with *E. coli* were generally applicable and in part to demonstrate that the invention can used effectively with respect to organisms, like the oral bacteria, for which relatively little sequence information is available. This part of the study strategy was designed to positively identify species using species-specific capture probes.

The GroEL gene was chosen because sequences for that gene were available from each of three target oral bacteria and for *E. coli*. In addition, GroEL sequences contain enough phylogenetic information for specific identification of target organisms. The primers that were designed are presented in Table 1. These primers yield specific PCR products from *E. coli*, *P. gingivalis*, and *H. actinomycetemcomitans*. These primers were found not to work for *T. denticola*, so a set of primers was chosen for that organism which were directed towards the FlgE gene. The table also sets forth the sequences used for capture probes used in the studies.

TABLE 1

Primer and Probe Sequences Used in Studies Herein

| Function | Species | Target | Sequence |
| --- | --- | --- | --- |
| PCR Primer | E. coli | GroEL | AAACGTGGTATCGACAAAGC (SEQ ID NO: 1) |
| PCR Primer | E. coli | GroEL | CGGTCGAACTGCATACCTTC (SEQ ID NO: 2) |
| Capture | E. coli | GroEL | TCAGTTCTTCAACTGCAGCGGTAA (SEQ ID NO: 3) |
| Capture | H. actinomycetemcomitans | GroEL | AGCTCGGCAACCACTGAGTTGA (SEQ ID NO: 4) |
| Capture | P. gingivalis | GroEL | GCGATGTGAGTTACCACAGCCTTTA (SEQ ID NO: 5) |
| PCR Primer | T. denticola | FlgE | AACGTAAATACAACAGGTTTT (SEQ ID NO: 6) |
| PCR Primer | T. denticola | FlgE | GTATACCTTAAATTCGGT (SEQ ID NO: 7) |

Using a 40° C. hybridization temperature in the PCR program, the E. coli primers shown will amplify the GroEL sequence from E. coli, H. actinomycetemcomitans, and P. gingivalis to yield a 242bp amplification product. The FlgE primers used with T. denticola yield a fragment of the size 542 bp. Once the GroEL primers have been used to amplify the sequences in the three species flanking the sequences to which the primers hybridize, the three bacterial species are differentiated from one another by the use of the three "capture probes" listed in the Table, which hybridize to regions in the amplified sequences which differ among the three species.

The PCR primer identified in Table 1 as SEQ ID NO 1 was synthesized with a fluorescein label attached. In the procedure set forth in Example 2, below, this permitted detection of the captured PCR product, which was labeled with fluorescein by the presence of the hybridized primer. The procedure could, of course, alternatively be conducted using a labeled signal oligo (an oligonucleotide capable of hybridizing to the expected PCR product and bearing a functional group for labeling), to permit detection of the PCR product, rather than a labeled PCR primer.

Example 2

These studies show the ability of the invention to determine differences in sensitivity to antibiotics between different strains of the same microorganism.

A nalidixic acid resistant strain of E. coli (ATCC number 27325, commonly referred to in the literature as strain W3110) and a nalidixic acid resistant strain (ATCC number 47056, commonly referred to as strain NK5830) were inoculated into L-broth in separate containers and cultured until early log phase (usually reached in E. coli in 1 to 1.5 hours). At 1.5 hours, the two cultures were inoculated into separate series of containers. Each series of containers was then divided into groups. Nalidixic acid was added to the first group of each series, to a final concentration of 100 μg/ml. Tetracycline was added to the second group of each series, to a final concentration of 100 μg/ml. No antibiotic was added to the third group of each series, which served as a control. All the cultures in each series were then incubated for a further hour, after which 100 mM of BrdU was added, and the cultures were permitted to incubate for an additional hour.

The cultures were then analyzed by the immunocapture system using either DNA purified by the method set forth in Example 1, above, or crude, sodium hydroxide lysates, prepared as follows. Each culture lysed by this method was mixed with 0.1 of its volume of 5 mg/ml lysozyme. After 5 minutes, a volume of 0.4M NaOH equal to the sample was added to simultaneously lyse the bacteria and to denature the DNA. Small portions (2–10 μl) of this lysate could be used directly in the immunocapture system so long as enough buffering capacity was available in the capture solution to neutralize the NaOH.

Figure 3:
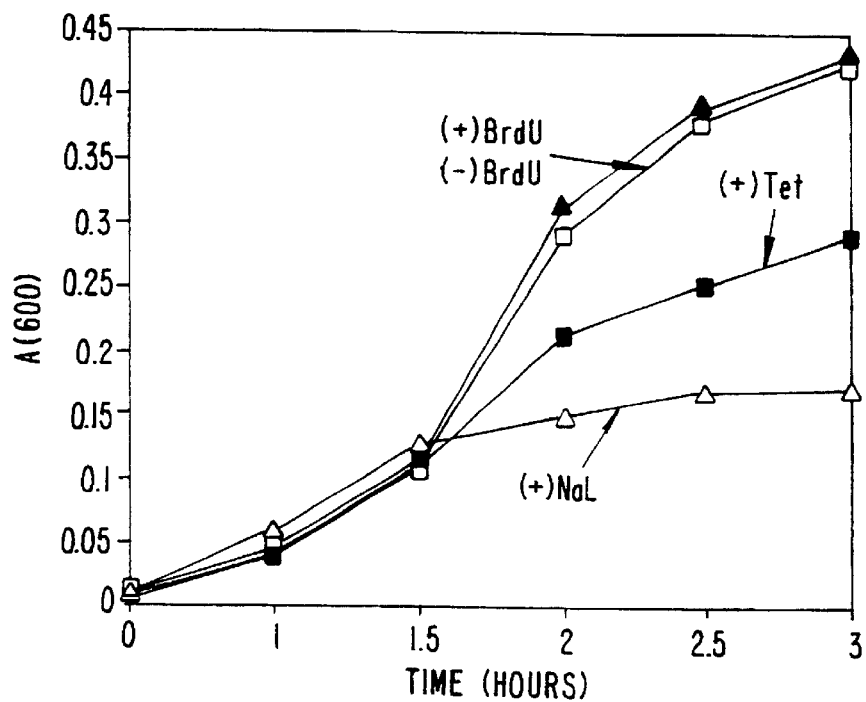
FIG. 3 shows growth curves for two strains of E. coli. The top graph shows the growth curve for wild type strain W3110, which is labeled "$NaL^{sens}$" to indicate that it is sensitive to the antibiotic nalidixic acid ("NaL"). The bottom graph shows the growth of the nalidixic acid resistant strain NK5830. For both graphs, the following icons are used. Filled squares: cultures grown in the presence of BrdU, with no antibiotics present. Diamonds: cultures grown in the absence of BrdU, with no antibiotics present. Filled triangles: cultures grown in the presence of tetracycline ("(+) Tet"). Hollow triangles: cultures grown in the presence of NaL ("(+)NaL").
Figure 3:
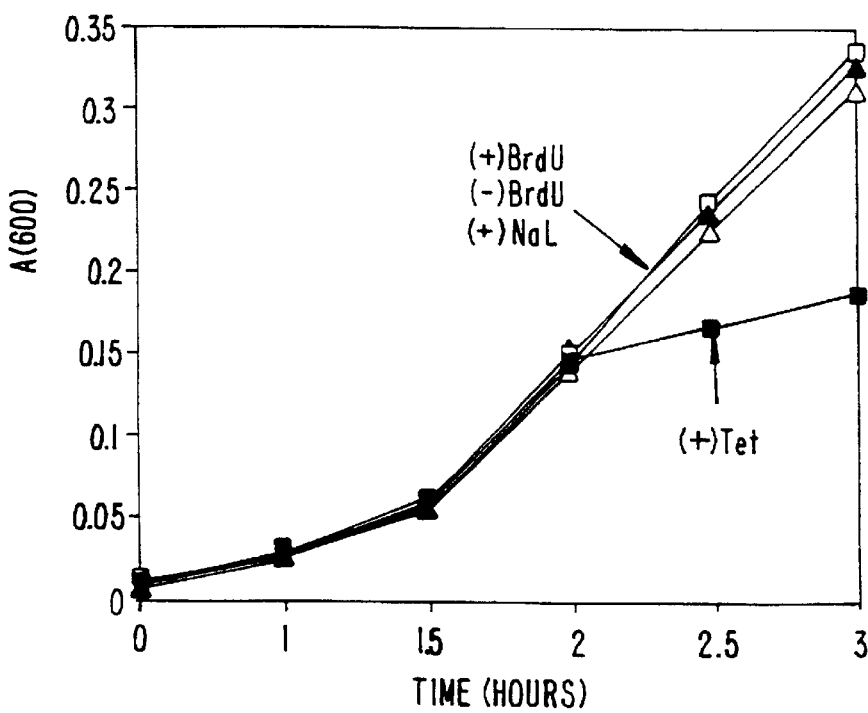

FIG. 3 shows growth curves for the two strains of E. coli used in this study. While the wild type strain W3110 began to reach saturation in 3 hours, either nalidixic acid or tetracycline inhibited growth. Addition of BrdU at 2.5 hours did not change the growth profile. In contrast, while the nalidixic acid resistant strain NK5830 also approached saturation at 3 hours (these cells grew more slowly than the wild type strain), addition of nalidixic acid did not cause any growth inhibition. However, these cells showed the same sensitivity to tetracycline as did strain W3110.

Figure 4:
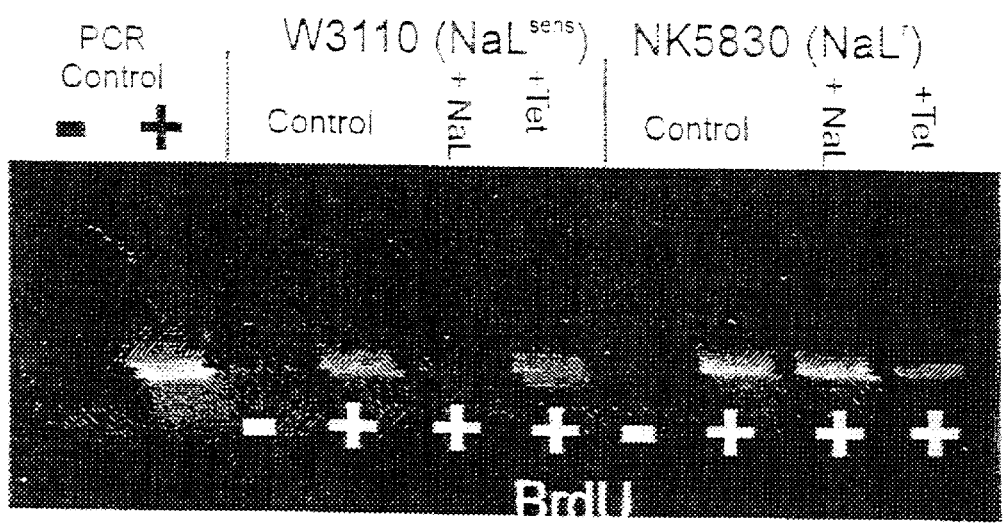
FIG. 4 shows the results of gel electrophoresis of DNA after PCR of two strains of E. coli with different sensitivities and resistances to antibiotics. The first two lanes in FIG. 4 are PCR controls, either without (−) or with (+) the addition of DNA. The two lanes designated "Control", under the title W3110, and the corresponding two lanes under the title NK5830, were immunocapture assay controls to which no antibiotic was added. The samples in the first of each of these pairs of lanes, labeled "−", had no BrdU added during cell growth. The second, +, lane in each of these pairs are from controls grown in the presence of BrdU in the medium. The next two lanes under each title indicate samples grown in the presence of either nalidixic acid (+Nal) or tetracycline (+Tet).

The results of the immunocapture studies are shown in FIG. 4. The first two lanes in FIG. 4 are PCR controls, either without (–) or with (+) the addition of DNA. The next two lanes designated "control", under the title W3110, and the corresponding two lanes under the title NK5830, were immunocapture assay controls to which no antibiotic was added. The samples in the first of each of these pairs of lanes, labeled "–", had no BrdU added during cell growth. These lanes show there was very low background with either E. coli strain. The second, +, lane in each of these pairs are from controls grown in the presence of BrdU in the medium. These lanes show a strong signal, demonstrating the vigorous growth of the cells in the presence of BrdU, but without the presence of any antibiotic.

The next two lanes under each title indicate samples grown in the presence of either nalidixic acid (+Nal) or tetracycline (+Tet). For W3110, the addition of nalidixic acid suppresses DNA synthesis and therefore leads to a loss of signal in the immunocapture. In contrast, NK5830 yielded a strong positive signal, consistent with the resistance of this strain to this antibiotic. In contrast, both strains yielded a significant positive signal when grown in the presence of tetracycline.

The PCR products were then detected. The list below sets forth the steps and reagents employed; the time for each step is set forth in the text following the list. All the steps were conducted in the wells of microtiter plates under constant mixing. The assay can also be performed without mixing the samples by suitably lengthening the incubation times for each step. Each of the following steps was performed by moving a streptavidin-coated dipstick from well to well.

| Step No. | Step Name | Volume | Procedure |
|---|---|---|---|
| Step 1 | Capture oligos | 200 µl | 200 ng/ml of biotin-labeled capture oligo in assay wash (0.1M sodium phosphate pH 8.0/0.5% Tween-20) were added. |
| Step 2 | Sample well | 200 µl | 2M guanidine thiocyanate in a base solution of 50 mM Tris (pH 8.0/10 mM EDTA/3% N-lauryl sarcosine/0/3% SDS was added. |
| Step 3 | Assay wash | 200 µl | |
| Step 4 | Assay Wash | 200 µl | |
| Step 5 | Conjugate | 200 µl | 2 ug/ml anti-fluorescein-HRP antibody conjugate in 50 mM Tris (pH 8.0)/0.1M NaCl/0.5% Triton X-100/2.2% Gelatin was added and incubated for 5 minutes. |
| Step 6 | Assay Wash | 200 µl | |
| Step 7 | Assay Wash | 200 µl | |
| Step 8 | Substrate | 200 µl | TMB in an appropriate buffer, as supplied by the vendor (Research Diagnostics, Inc., NJ) was added. |

Ten µl of each sample of the post PCR products were heated to 95° C. for 2 minutes and added to the first well of the microtiter plate, containing 2M guanidine thiocyanate. A capture probe specific for *E. coli* (SEQ ID NO 3) was used to detect the presence of PCR product. Capture probes were adsorbed for 10 minutes, hybridization was performed for 10 minutes, and signal probe hybridization was performed for 10 minutes. After a 1 minute wash, conjugate was adsorbed for 5 minutes. Following 2 more washes, the substrate reaction was run for 8 minutes. Blue color in the wells was read at 650 nm.

Figure 5:
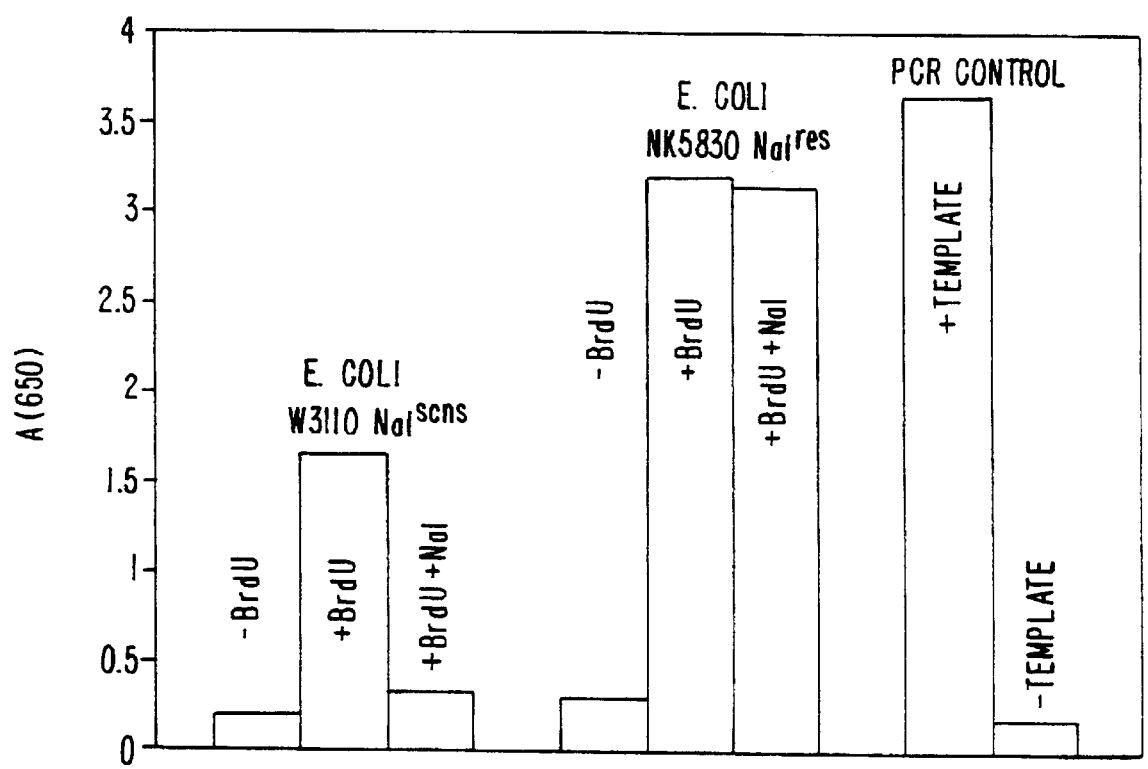
FIG. 5 shows a colorimetric analysis of PCR products of two E. coli strains in a colorimetric sandwich assay. PCR products were heated to 95° C. for 2 minutes and added to the reagent plate. A capture probe specific for E. coli (see Table 1, infra) was used to detect the presence of PCR product. Results were read at 650 nm. Strain W3110 is sensitive to NaL ("$Nal^{sens}$"); strain NK5830 is resistant to Nal ("$Nal^{res}$"). The lanes marked "−BrdU" represent negative controls grown in the absence of BrdU, lanes marked "+BrdU" indicate cultures grown in its presence. "+Nal" indicates cultures grown in the presence of NaL. The lanes marked "+Template" and "−Template" are PCR controls.

The results are shown in FIG. 5. They follow closely the gel analysis shown in FIG. 4. The results with nalidixic acid demonstrate how effectively antibiotic sensitive and resistant organisms can be differentiated using the invention.

Example 3

This example shows that the invention can be used to detect antibiotic-resistant microorganisms in a mix with antibiotic-susceptible organisms of the same species.

In these studies, the nalidixic acid-resistant *E. coli* strain NK5830 was mixed with the nalidixic acid-sensitive strain W3110 in various proportions. Saturated overnight mixed cultures were diluted in fresh L-broth at 1:100, to a total inoculum volume of 401 µl. Cells were then grown for 1.5 hours, and nalidixic acid was added. After incubation for 1 more hour, BrdU was added and growth continued for 30 minutes. The immunocapture experiment was then performed on either purified DNA or on crude sodium hydroxide lysates.

Figure 6:
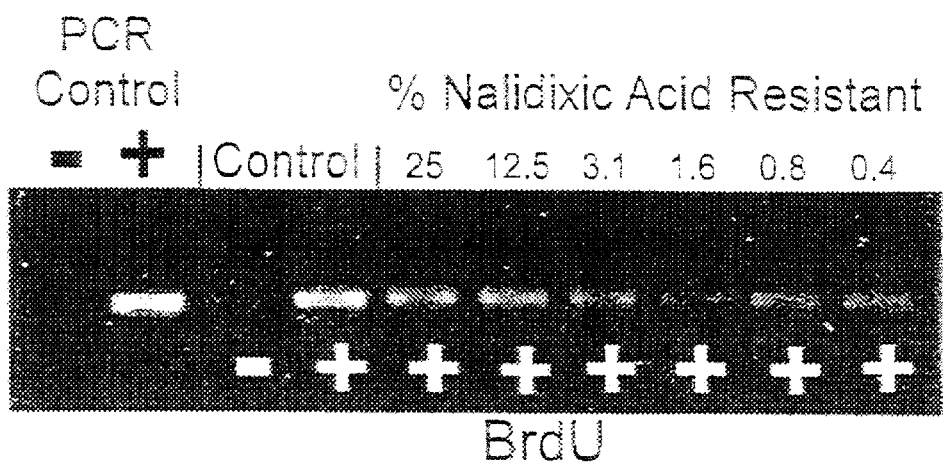
FIG. 6 shows results of studies in which antibiotic-resistant and antibiotic-sensitive organisms of the same species were mixed in cultures with decreasing percentages of the resistant organisms. The first two lanes are PCR controls, either without (−) or with (+) the addition of DNA. The next two lanes designated "control," were immunocapture assay controls to which no antibiotic was added. The samples in the first control lane, labeled "−", had no BrdU added during cell growth. The second, +, lane is from a control grown in the presence of BrdU in the medium. The next lanes show the results in which the indicated percentages of the nalidixic acid resistant strain NK5830 were present in mixed culture with the nalidixic acid sensitive strain W3110.

The results are presented in FIG. 6. The first two lanes are again the PCR controls, either without (−) or with (+) the addition of DNA. The next two lanes designated "control," were immunocapture assay controls to which no was added. The samples in the first control lane, labeled "−", had no BrdU added during cell growth. This lane shows the presence of very low background. The second, +, lane is from a control grown in the presence of BrdU in the medium. This lane shows a strong signal, demonstrating that the organism grew vigorously in the presence of BrdU when no antibiotic was present.

The next lanes show the ability of the assay to detect the nalidixic acid resistant strain when mixed in various proportions with the nalidixic acid sensitive strain. The results demonstrate that resistant organisms could be detected even at 0.4%, the lowest level tested.

The invention was also used to determine the sensitivity of *E. coli* to a number of antibiotics. The antibiotics which showed the greatest effect on the growth of *E. coli* in these assays were nalidixic acid, rifampicin, and gentamycin. Chloramphenicol exhibited a significantly reduced growth compared to controls grown for the same period in the absence of the antibiotic. Streptomycin and tetracycline showed little or no effect. Ampicillin lysed *E. coli* strain W3110; therefore the effect of the ampicillin was demonstrated by the lack of detectable BrdU compared to the control.

Example 4

This example shows the use of the invention to determine the sensitivity of oral bacteria to a number of antibiotics.

A. Studies on *Porphyromonas gingivalis*

A saturated culture of *Porphyromonas gingivalis* (ATCC No. 33277) grown anaerobically (85% nitrogen/5% carbon dioxide/10% hydrogen) was diluted 1:10 in fresh modified ETSB media (see Syed, S. A., J. Clin. Microbiol. 11:522–526 (1980)) with added hemin, and incubated 6 hours anaerobically. The culture was then divided into aliquots. A suitable number of the aliquots were reserved as controls and incubated without having an antibiotic added to the medium. The remaining, test aliquots had added to the medium one of the following three antibiotics: metronidazole, nalidixic acid, or tetracycline. All the aliquots were then incubated anaerobically for an additional 2 hours.

Following this 2 hour incubation, BrdU was added to each tube and incubation was continued for an additional 2 hours. The bacterial culture was then lysed either by the chemical disruption or the crude NaOH lysate methods set forth above and an immunocapture performed with anti-BrdU antibodies. PCR was then performed according to the protocol set forth in the Examples above. The samples were run using a capture probe specific for *P. gingivalis*, set forth in Table 1.

Figure 7:
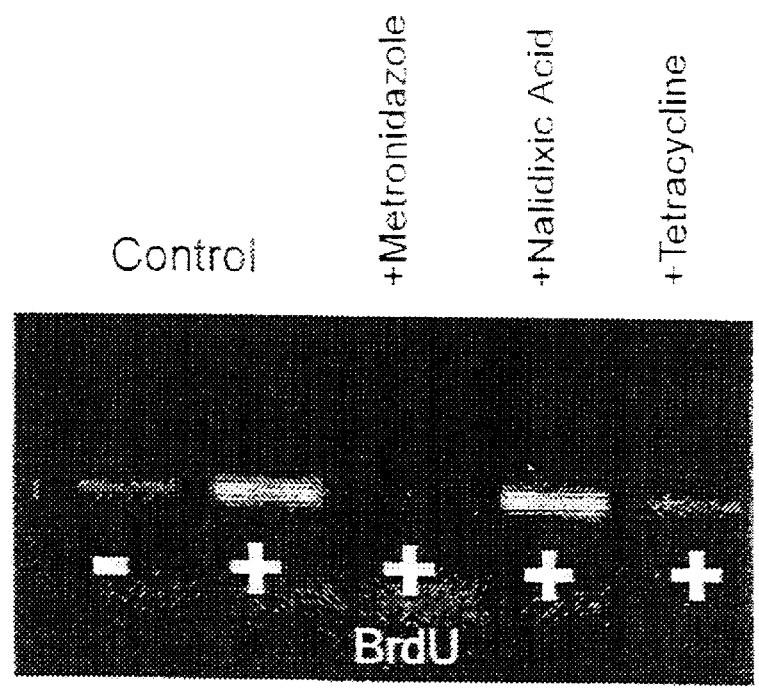
FIG. 7 shows the effect of antibiotics on the growth of the oral bacteria Porphyromonas gingivalis by gel electrophoresis of PCR products. The first two lanes are control cultures grown in the absence ("−") or presence ("+") of BrdU. The next three lanes show the results from cultures grown in the presence of metronidazole, nalidixic acid, or tetracycline, respectively.

The results are presented in FIG. 7. They demonstrate that *P. gingivalis* is sensitive to tetracycline and metronidazole, but resistant to nalidixic acid. The test clearly shows the metronidazole sensitivity and the nalidixic acid resistance of this strain of *P. gingivalis*. Metronidazole and nalidixic acid are DNA synthesis inhibitors which have different mechanisms of inhibition. The culture grown on tetracycline yielded a light signal, and further work will be needed to determine if this signal indicates that the organism is sensitive (when compared to the controls) or resistant (since a light positive was obtained) to this antibiotic.

B. Studies on *Haemophilus actinomycetemcomitans*

*H. actinomycetemcomitans* is reported to be a human pathogen, and has been implicated in juvenile periodontitis. In these studies, a culture of *H. actinomycetemcomitans* (ATCC No. 43718; previously known as *Actinobacillus actinomycetemcomitans*) was grown to saturation under anaerobic conditions as in part A, above, except that hemin was not added to the medium. The culture was diluted 1:10 into fresh media, and grown for a further 4 hours under anaerobic conditions. At this point, the culture was divided into aliquots and subjected to the same testing protocol as was employed in part A of this Example, except that after the BrdU was added, the 2 hour incubation was followed for convenience by overnight storage under refrigeration at 4° C. The next day, the aliquoted cultures were lysed by the NaOH lysis protocol described above, PCR was performed, and the capture probe set forth in Table 1 for this organism was employed.

Figure 8:
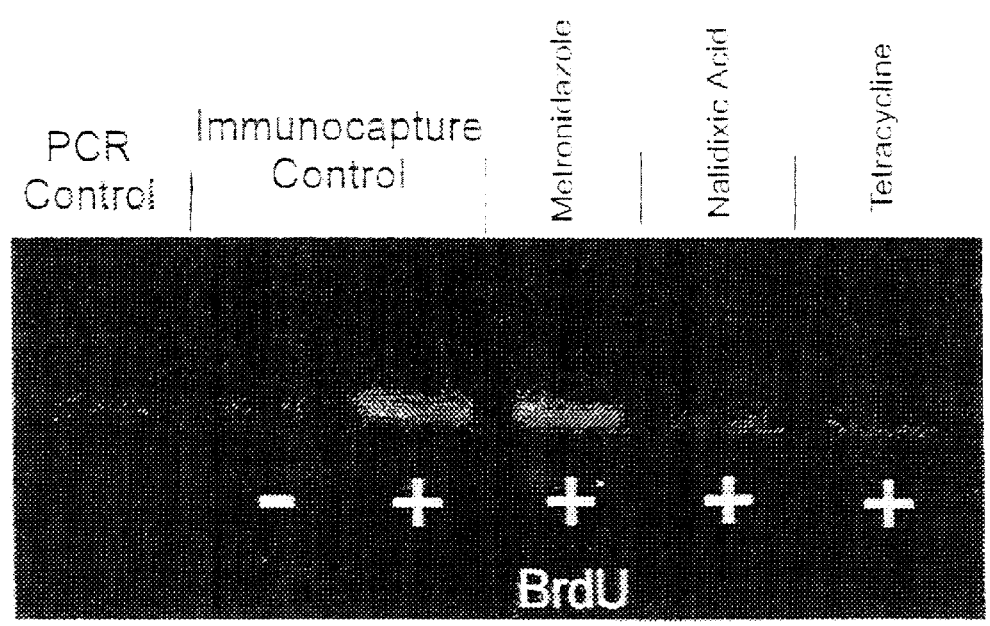
FIG. 8 shows the effect of antibiotics on the growth of the oral bacterium H. actinomytemcomitans by gel electrophoresis of PCR products. The first lane is a PCR control to show background. The two lanes marked "Immunocapture controls" are control cultures grown in the absence ("−") or presence ("+") of BrdU. The next three lanes show the results from cultures of the organism grown in the presence of metronidazole, nalidixic acid, or tetracycline, respectively.

The results are shown in FIG. 8. In these assays, *H. actinomycetemcomitans* showed sensitivity to nalidixic acid and tetracycline, and resistance to metronidazole. This is in accord with the literature, which reports that this organism does not have the enzymatic activity necessary for metabolic activation of metronidazole.

C. Studies with *Treponema denticola*

*Treponema denticola* was also studied using the invention. In these studies, a culture of *T. denticola* (ATCC number 35405) was inoculated into fresh media and grown anaerobically for 1 day in NOS media (ATCC media formulation 1494). The cultures were grown as in Part A of this Example, except that the cultures were incubated for about 8 hours prior to the addition of BrdU, they were incubated overnight after the addition of BrdU, and the samples were analyzed the next day. The PCR was conducted in the manner described above, except that a GroEL primer set was not available and a primer set for the FlgE gene (endoflagellar subunit protein) referred to FlgE001 and FlgE006 was substituted. These primers were expected to give rise to a 542 bp PCR fragment.

Figure 9:
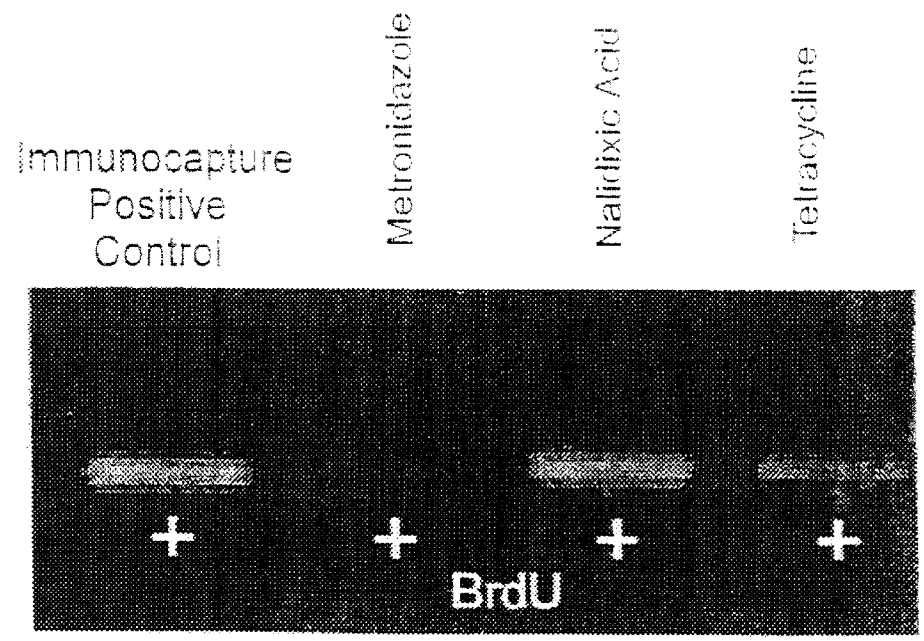
FIG. 9 shows the effect of antibiotics on the growth of the oral bacterium Treponema denticola by gel electrophoresis of PCR products. The first lane is an immunocapture control grown in the presence ("+") of BrdU. The next three lanes show the results from cultures of the organism grown in the presence of metronidazole, nalidixic acid, or tetracycline, respectively.

The results of the assay are presented in FIG. 9. They show that *T. denticola* is sensitive to metronidazole and tetracycline, but resistant to nalidixic acid. Due to an experimental error, a negative immunocapture control was not available. However, the metronidazole results show that the level of BrdU incorporation is at background, that is, that the organism showed no detectable growth in the presence of the antibiotic. In contrast, with nalidixic acid, a signal was obtained that was equivalent to the positive control. Since a negative capture control was not available for this experiment, it was harder to interpret the tetracycline result. However, it appears that tetracycline affects BrdU incorporation into *T. denticola* DNA.

The ability to study the susceptibility of this organism to antibiotics by means of the invention is particularly exciting since susceptibility testing of the treponemes using standard methods is difficult. Its success here reflects the very powerful nature of the invention for antibiotic susceptibility testing. Additionally, this study demonstrates that the assay can be conducted without optimizing the assay for the particular organism. Persons of skill in the art will recognize, however, that the time needed to conduct the assay can be minimized by determining the optimum times for performing the various steps, such as the addition of the antibiotic or of the BrdU, with respect to the particular microorganism of interest. Such determinations can be readily made by persons of skill in the art.

Example 5

This Example demonstrates the use of the invention to detect the presence of a bacterium present in small numbers in a mixed culture with far larger numbers of another bacterial species.

A. Detection of *P. mirabilis* in a mixed culture with *E. coli*

In this experiment, antibiotics were not used since we wished to investigate whether a fast growing species could overgrow and could "swamp out" the detection of the slower growing species. *Proteus mirabilis* was chosen as the slow growth species. Equivalent nucleoside incorporation requires about 2.5 times more time in *P. mirabilis* as it does in *E. coli*. Therefore, it is easy to prepare cultures overgrown with *E. coli*. In this experiment, saturated overnight cultures of *E. coli* C600 and *P. mirabilis* were inoculated into L-broth in various ratios (100:1, 50:1, 25:1, 12.5:16:1, 3:1, 1.5:1 volume ratios of *E.coli:P. mirabilis*). These were incubated with shaking for 90 minutes at 37° C. (at 90 minutes under these conditions, *E. coli* enters log phase growth), after which BrdU was added to a concentration of 1mM and the cells allowed to incubate for 30 minutes. One ml of cells was pelleted and the total DNA was extracted and resuspended in 0.1 ml of water.

Ten percent of the DNA of each sample was subjected to the Immunocapture assay. Replicates of each sample were run, with one set being amplified using the *E. coli* GroEL primers, and the other sample using the *P. mirabilis* lpp primers. A light signal for *P. mirabilis* could be detected in the 100:1 culture of *E. coli* to *P. mirabilis*, and thus 1:100 is the nominal sensitivity of the assay. At the other ratios, *P. mirabilis* was identified with a strong signal over *E. coli*.

The results showed the *P. mirabilis* lpp primers were specific in amplifying *P. mirabilis* in the presence of *E. coli*. Further, the results showed that the invention was able to detect a target organism present in a mixed culture at a concentration of 1% of a second organism. The results further showed that the GroEL primers amplified *P. mirabilis* as well as *E. coli*. This did not affect the results of these studies, since the question was whether *P. mirabilis* present in a small percentage could be detected. These results do, however, suggest that it is desirable to design the experiments so that the non-specific amplification of an organism not of interest will not interfere with the interpretation of the results. This can be accomplished, in part, by careful primer selection. The GroEL primers used in this study are set forth in Example 1, Table 1. The lpp primers used are set forth in Table 2, infra.

B. Studies using Antibiotic-resistant and Antibiotic-sensitive Strains in a Mixed Culture We also measured the effect of having a large population of antibiotic resistant bacteria on the ability of the invention to detect susceptible cells and determined whether the presence of a large excess of an ampicillin resistant strain created permissive conditions which would allow growth of the ampicillin susceptible species. The *P. mirabilis* strain used in these studies was found to be resistant to ampicillin at over 400 µg/ml. A strain of *E. coli* (C600) was chosen that is extremely sensitive to ampicillin.

Starting with saturated overnight cultures of both *P. mirabilis* and *E. coli*, 50:1 ratios (100 µl *P. mirabilis*+2 µl *E. coli*) were prepared and inoculated into L-broth supplemented with 5, 10, or 20 µg/ml ampicillin. A control without ampicillin was also run. After a 2 hour incubation, BrdU was added to 1 mM and the incubation then continued for an additional hour. Cells were harvested and DNA was purified from 1.5 ml of each culture and suspended in 200 µl water. Ten µl of the suspension were denatured with 10 µl of 0.4M NaOH. Ten µl of this mix were added to 200 µl of diluted antibody. After 15 minutes, 100 µl of the antibody complexes were adsorbed to Protein A coated tubes. After washing the tubes, the PCR master mix which contained PCR primers for the FlaA gene was added. (The FlaA primers used are set forth in Table 2, infra.)

FlaA amplifies both organisms, but yields a 1 kb PCR product when amplifying *E. coli* and a 800 bp PCR product when amplifying *P. mirabilis*. The only sample which gave both the *E. coli* and *P. mirabilis* products was the sample in which the organisms were grown in the absence of ampicillin. All of the others had only the *P. mirabilis* PCR product. These data demonstrate that a vast excess of ampicillin resistant *P. mirabilis* cells did not affect the antibiotic susceptibility of the the sensitive *E. coli* strain or eliminate enough ampicillin for the sensitive strain to grow.

TABLE 2

The lpp and FlaA primers used in this Example*

| Function | Species | Target | Sequence |
|---|---|---|---|
| PCR Primer | Proteus mirabilis | lpp | CTGGCTTCAGGCCTATTAGC (SEQ ID NO:8) |
| PCR Primer | Proteus mirabilis | lpp | TGCTTAATAAGCTGAAAACG (SEQ ID NO:9) |
| PCR Primer | E. coli/P. mirablis | FlaA | ATGGGCGATAGTATTCTTTCT (SEQ ID NO:10) |
| PCR Primer | E. coli/P. mirabilis | FlaA | TCATTTGGGCTGTTCCTCGTTCAG (SEQ ID NO:11) |

*The P. mirabilis lpp primers yield a 240 bp product. The FlaA primers yield a 1 kb product from E. coli and an 800 bp product from P. mirabilis.

Example 6

This Example demonstrates the use of the invention to study slow growing bacteria such as mycobacteria.

A. Incorporation of BrdU by Mycobacteria.

Cells in the M. tuberculosis complex grow very slowly, with a doubling time on the order of 20–30 hours. Given the lipid-rich, relatively impermeable cell walls typical of mycobacteria, we wanted to determine whether these cells would take up and incorporate BrdU over a reasonable period of time.

Time course experiments were performed using M. bovis BCG, an avirulent member of the M tuberculosis complex. An early stationary phase culture was diluted 4-fold into two flasks containing Dubos broth with albumin enrichment and glycerol. BrdU was added to one of the flasks until a concentration of 5 MM was reached, and cultures were incubated on a shaker at 37° C. under 5% $CO_2$. Samples were taken immediately upon BrdU addition on day zero, and on days 1, 2, 4, and 5 following BrdU addition. The samples were lysed by an enzymatic method resulting in a lysate in concentrated guanidine thiocyanate. DNA was extracted from frozen guanidine lysates using a non-phenolic IsoQuick kit (Orca Research, Bothell, Wash.). Extracted DNA was heat denatured and mixed with an anti-BrdU antibody (Sigma Chemical Co., St. Louis, Mo.) in a Tris-BSA buffer. After a 15 minute incubation at room temperature, the mixture was transferred to a tube precoated with Protein A. After a 15 minute adsorption step, the tubes were washed twice with a Tris/Tween buffer, and twice with 0.1 M Tris pH 7.5. A PCR master mix containing primers directed towards the 16 s rRNA gene was added to each tube. After thermocycling, results were visualized by gel electrophoresis on 1.5% agarose gels.

All samples were also amplified without immunocapture to demonstrate that all samples had DNA, and that the amounts of DNA that went into each immunocapture were about the same. The results of the immunocapture experiment reveals that BrdU labeled DNA could be detected in as few as 2 days after treatment with BrdU. Increasing amounts of labeled DNA were seen in the samples from days 4 and 5, indicating that incubation for those periods provides more sensitive detection of the organism. Thus, the longer period of incubation is preferred if speed is not critical to the particular purpose for which the assay is being run.

B. Ability of the Invention to Determine whether Antibiotics Interfere with BrdU Incorporation by Mycobacteria.

We tested the ability of various first-line antibiotics to affect BrdU incorporation into DNA. The antibiotics were Isoniazid,™ a mycolic acid (cell wall) synthesis inhibitor, ciprofloxacin, a quinolone drug that acts directly on DNA replication, rifampin, an RNA polymerase inhibitor, and streptomycin, a translational inhibitor. A four day protocol and a seven day protocol were tested. In the four day protocol, on Day 0, stationary cultures of M. bovis BCG were diluted into Dubos broth containing the antibiotic being tested. On Day 2, BrdU was added, and on Day 4, cells were harvested. In the seven day protocol, on Day 0, cultures were diluted in Dubos with the antibiotic. BrdU was added on day 4, and cells were harvested on Day 7. Controls were cultures grown without the addition of antibiotics. In control experiments, samples were amplified to confirm that they all had DNA, and that approximately equal amounts of DNA were in each sample.

The results showed that each antibiotic inhibited incorporation of BrdU into DNA in both the four day and the seven day protocol. The seven day protocol yielded a darker gel band, apparently because the extra 3 days of growth increased the cell mass of the culture and the extent of labeling. We also determined in the course of the experiments that if it was desired to increase the sensitivity of the assay, a larger proportion of the DNA in the cultures for the immunoassay could be used and a larger proportion of the PCR mix could be loaded onto the gels used for electrophoresis.

Example 7

This Example studies the effects of varying the assay by pH of the capture buffer for pH, the presence or absence of detergents, and the concentration of salts.

A. Studies to Optimize pH

Immunocapture buffers of varying base buffer composition were prepared and tested for efficientcy of immunocapture and for background binding. Base buffers for formulating the binding buffer are chosen based on the equivalence point of the buffer, that is, the pH at which the compound has maximal buffering capacity. For Tris, that pH is around 8; the useful buffering range is from about pH 7.5 to pH 8.5. For phosphate buffered saline, the maximal buffering capacity is about pH 6.8, with a useful range of about pH 7.5 to about pH 6.5. Tris was tested at pH 8.3 and pH 7.5 and phophate buffer was tested at pH 7.0 and 6.5. DNA (500 ng, 50 ng, and 5 ng) was denatured in 5 µl total volume 0.2M NaOH. The DNA solution was added to the base buffer being tested +1% bovine serum albumin +2.5mM EDTA +0.1% Tween 20 and anti-BrdU antibody (Sigma) at a 1:200 dilution. The results showed that at pH 8.3, considerable background binding was obtained, that is, there was very little discrimination between BrdU labeled and un-labeled DNA. At pH 7.0 and pH 6.5, background was lower but the assay was less sensitive. For all levels of input DNA, signal intensities were lower. The results indicate that 0.2M Tris-Cl pH 7.5 was the best buffer.

2. Studies to Optimize Presence of Detergent.

Inclusion of 0.1% Tween 20 in the immunocapture buffer significantly reduced the background.

3. Studies to optimize salt concentration.

Binding buffers were prepared containing 50 mM, 100 mM, and 200 mM NaCl. The base buffer was 0.2M Tris, pH 7.5. The amount of DNA was varied from 500 ng to 5 ng. Results were assessed for background and sensitivity. Signal intensity appreared to be inversely proportional to salt concentration. At 50 mM, a significant reduction in background was observed, with only a slight decrease in sensitivity. We concluded that the optimal binding buffer has a composition of 0.2M Tris pH7.5, 1% BSA, 0.1% Tween 20, 2.5 mM EDTA, and 25 or 50 mM NaCl.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An assay for determining the identity of an unknown live microorganism in a mixed culture, said assay comprising the steps of:
   i. culturing a sample of the mixed culture in an aqueous medium, said medium able to culture one or more microorganisms other than the unknown microorganism and comprising a nucleic acid analog, which analog (a) can bind to an analog-specific binding member, (b) can enter living cells of the unknown microorganism from said medium, (c) once inside a living cell, can be incorporated into nucleic acids of replicating cells of the unknown microorganism, and (d) is not toxic to cells of the microorganism when incorporated into said nucleic acids at concentrations sufficient to permit detection;
   ii. lysing cultured microorganisms to release nucleic acids of the unknown microorganism, and of other microorganisms present;
   iii. capturing nucleic acids incorporating the analog using the analog-specific binding member;
   iv. separating the captured nucleic acids from any nucleic acids which have not been captured;
   V. amplifying captured nucleic acids originating from the unknown microorganism; and,
   vi. detecting amplified captured nucleic acids originating from the unknown microorganism and identifying the unknown microorganism from which the amplified captured nucleic acids originate.

2. An assay of claim 1 wherein step (v) is a selective amplification of a subset of the captured nucleic acids.

3. An assay of claim 1 wherein the identity of the microorganism in step (vi) is determined by hybridization of the amplified captured nucleic acids to a species-specific nucleic acid sequence.

4. An assay of claim 1 wherein the unknown microorganism is a bacterium.

5. An assay of claim 1 wherein the unknown microorganism is a pathogen.

6. An assay of claim 5 wherein the pathogen is a pathogen of a mammal.

7. An assay of claim 5 wherein the pathogen is a virus.

8. An assay of claim 5 wherein the pathogen is a fungus.

9. An assay of claim 5 wherein the pathogen is a protozoan.

10. An assay of claim 1 wherein the mixed culture is of two or more strains of the same species of microorganism.

11. An assay of claim 1 wherein the analog is bromodeoxyuridine.

12. An assay of claim 11 wherein the analog-specific binding member is an antibody.

13. An assay of claim 1 wherein the aqueous medium further comprises an antibiotic.

14. An assay for determining the identity of an unknown live microorganism in a sample of a mixed culture, which microorganism is a virion or other microorganism which cannot replicate outside of a living cell, said assay comprising the steps of:
   i. culturing said sample in a cell in an aqueous medium, said medium comprising a nucleic acid analog, which analog (a) can bind to an analog-specific binding member, (b) can enter living cells in which the unknown microorganism is being cultured, (c) once inside a living cell, can be incorporated into nucleic acids of replicating cells or virions of the unknown microorganism, and (d) is not toxic to cells or virions of the unknown microorganism when incorporated into said nucleic acids at concentrations sufficient to permit detection;
   ii. lysing cultured microorganisms to release nucleic acids of the unknown microorganism, and of other microorganisms present;
   iii. capturing nucleic acids incorporating the analog using the analog-specific binding member;
   iv. separating the captured nucleic acids from any nucleic acids which have not been captured;
   v. amplifying captured nucleic acids originating from the unknown microorganism; and,
   vi. detecting amplified captured nucleic acids originating from the unknown microorganism and identifying the unknown microorganism from which the amplified captured nucleic acids originate.

15. An assay of claim 14 wherein step (v) is a selective amplification of a subset of the captured nucleic acids.

16. An assay of claim 14 wherein the identity of the microorganism in step (vi) is determined by hybridization of the amplified captured nucleic acids to a species-specific nucleic acid sequence.

17. An assay of claim 14, wherein the unknown microorganism is a pathogen.

18. An assay of claim 17 wherein the pathogen is a pathogen of a mammal.

19. An assay of claim 18 wherein the pathogen is a virus.

20. An assay of claim 14, wherein the mixed culture is of two or more stains of the same species of microorganism.

21. An assay of claim 14, wherein the analog is bromodeoxyuridine.

22. An assay of claim 14 wherein the specific binding member is an antibody.

23. An assay of claim 14 wherein the aqueous medium further comprises an antibiotic.

24. An assay for determining the ability of a selected microorganism in a mixed culture to replicate in the presence of a selected chemical agent comprising the steps of:
   (i) providing a first mixed culture, comprising (a) a first aqueous medium or first cell culture which first aqueous medium or first cell culture is able to culture the selected microorganism and one or more microorganisms other than the selected microorganism, (b) a mixed culture comprising the selected microorganism and (c) a nucleic acid analog, which analog (I) can bind to an analog-specific binding member, (II) can enter living cells of the unknown microorganism from said medium or, in the case of a virion or other microorganism unable to replicate outside a living cell, can enter living cells in which the virion or other microorganism is being cultured, (III) once inside a living cell, can be incorporated into nucleic acids of replicating cells or virions of the unknown microorganism, and (IV) is not toxic to cells or virions of the microorganism when incorporated into said nucleic acids at concentrations sufficient to permit detection;
   (ii) adding said selected chemical agent to said first mixed culture;
   (iii) lysing the microorganisms in said first mixed culture to release nucleic acids of the selected microorganism, and of other microorganisms present,
   (iv) capturing from said first mixed culture nucleic acids incorporating the analog using the analog-specific binding member;
   (v) separating the captured nucleic acids from any nucleic acids which have not been captured;

(vi) amplifying captured nucleic acids originating from the selected microorganism;

(vii) detecting the presence or absence of amplified captured nucleic acids; and (viii) determining the ability of the selected microorganism to replicate in the presence of the selected chemical agent, wherein detecting the presence of said amplified captured nucleic acids in step (vii) indicates that the selected microorganism does have the ability to replicate in the presence of the selected chemical agent, while detecting the absence of said amplified captured nucleic acids in step (vii) indicates the selected microorganism does not have the ability to replicate in the presence of the selected chemical agent.

25. An assay of claim 24, further comprising (i) providing a second mixed culture, comprising (a) an aqueous medium or second cell culture which second aqueous medium or second cell culture is identical to said first aqueous medium or first cell culture, (b) a mixed culture comprising said selected microorganism, and (c) a nucleic acid analog, which analog (I) can bind to an analog-specific binding member, (II) can enter living cells of the unknown microorganism from said medium or, in the case of a virion or other microorganism unable to replicate outside a living cell, can enter living cells in which the virion or other microorganism is being cultured, (III) once inside a living cell, can be incorporated into nucleic acids of replicating cells or virions of the unknown microorganism, and (IV) is not toxic to cells or virions of the microorganism when incorporated into said nucleic acids at concentrations sufficient to permit detection;

(ii) lysing the microorganisms in said second mixed culture to release nucleic acids of the selected microorganism, and of other microorganisms present;

(iii) capturing nucleic acids incorporating the analog using the analog-specific binding member;

(iv) separating the captured nucleic acids of (iii) from any nucleic acids which have not been captured;

(v) amplifying captured nucleic acids of (iv) originating from the selected microorganism;

(vi) detecting the presence or absence of amplified captured nucleic acids of (v);

(vii) comparing the presence or absence of amplified captured nucleic acids detected from said second mixed culture with the presence or absence of amplified captured nucleic acids detected from said first mixed culture, and (viii) determining the ability of the selected microorganism to replicate in the presence of the selected chemical agent, wherein detecting the presence of amplified captured nucleic acids from the selected microorganism cultured in said first mixed culture and detecting the presence of amplified captured nucleic acids from the selected microorganism cultured in said second mixed culture indicates that the microorganism has the ability to replicate in the presence of the selected chemical agent, while detecting the absence of amplified captured nucleic acids from the selected microorganism cultured in said first mixed culture and detecting the presence of amplified captured nucleic acids from the selected microorganism cultured in said second mixed culture indicates that the selected microorganism does not have the ability to replicate in the presence of the selected chemical agent.

26. An assay of claim 24 wherein the amplifying of step (v) is by polymerase chain reaction.

27. An assay of claim 24 wherein the analog-specific binding member is attached to a solid support.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Escherichia
      coli GroEL PCR primer

<400> SEQUENCE: 1
aaacgtggta tcgacaaagc                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Escherichia
      coli GroEL PCR primer

<400> SEQUENCE: 2
cggtcgaact gcataccttc                                                    20

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Escherichia
      coli GroEL capture probe

<400> SEQUENCE: 3
tcagttcttc aactgcagcg gtaa                                               24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Haemophilus
      actinomycetemcomitans GroEL capture probe

<400> SEQUENCE: 4
agctcggcaa ccactgagtt ga                                                 22

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Porphyromonas gingivalis GroEL capture probe

<400> SEQUENCE: 5
gcgatgtgag ttaccacagc cttta                                              25
```

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Treponema
      denticola FlgE PCR primer

<400> SEQUENCE: 6
aacgtaaata caacaggttt t                                              21

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:Treponema
      denticola FlgE PCR primer

<400> SEQUENCE: 7
gtatacctta aattcggt                                                  18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Proteus
      mirabilis lpp PCR primer

<400> SEQUENCE: 8
ctggcttcag gcctattagc                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Proteus
      mirabilis lpp PCR primer

<400> SEQUENCE: 9
tgcttaataa gctgaaaacg                                                20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:Escherichia
      coli/Proteus mirabilis FlaA PCR primer

<400> SEQUENCE: 10
atgggcgata gtattctttc t                                              21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Escherichia
      coli/Proteus mirabilis FlaA PCR primer

<400> SEQUENCE: 11
tcatttgggc tgttcctcgt tcag                                           24
```